US006593374B2

(12) United States Patent
Pinney et al.

(10) Patent No.: US 6,593,374 B2
(45) Date of Patent: Jul. 15, 2003

(54) TUBULIN BINDING LIGANDS AND CORRESPONDING PRODRUG CONSTRUCTS

(75) Inventors: Kevin G. Pinney, Hewitt, TX (US); Vani P. Mocharla, Waco, TX (US); Zhi Chen, Hamden, CT (US); Charles M. Garner, McGregor, TX (US); Anjan Ghatak, Waco, TX (US); James M. Dorsey, Waco, TX (US)

(73) Assignee: Baylor University, Waco, TX (US)

( * ) Notice: Subject to any disclaimer, the term of this patent is extended or adjusted under 35 U.S.C. 154(b) by 137 days.

(21) Appl. No.: 09/804,280

(22) Filed: Mar. 12, 2001

(65) Prior Publication Data

US 2002/0055643 A1 May 9, 2002

Related U.S. Application Data

(60) Provisional application No. 60/188,295, filed on Mar. 10, 2000.

(51) Int. Cl.⁷ .................. A61K 31/075; C07C 41/00; C07C 215/00; C07F 9/02

(52) U.S. Cl. .................. 514/721; 568/633; 564/443; 558/197

(58) Field of Search .................. 568/633; 514/721; 564/443; 558/197

(56) References Cited

U.S. PATENT DOCUMENTS

| | | | | |
|---|---|---|---|---|
| 4,233,814 A | | 11/1980 | Jones et al. ............ 260/326.55 |
| 4,996,237 A | * | 2/1991 | Pettit et al. ................. 514/720 |
| 5,342,547 A | | 8/1994 | Konya et al. | |
| 5,409,953 A | * | 4/1995 | Pettit et al. ................. 514/464 |
| 5,525,632 A | | 6/1996 | Obsumi et al. | |
| 5,561,122 A | * | 10/1996 | Pettit et al. ................. 514/130 |
| 5,596,106 A | | 1/1997 | Cullinan et al. .............. 549/57 |
| 5,596,786 A | * | 1/1997 | Pettit et al. ................. 568/646 |
| 5,674,906 A | | 10/1997 | Hatanaka et al. | |
| 5,731,353 A | | 3/1998 | Obsumi et al. | |
| 5,886,025 A | | 3/1999 | Pinney ........................ 514/443 |
| 5,958,916 A | | 9/1999 | Bryant et al. | |
| 6,030,986 A | | 2/2000 | Palkowitz ................... 514/324 |
| 6,040,309 A | | 3/2000 | Dack et al. ................. 514/253 |
| 6,048,875 A | | 4/2000 | De Manteuil et al. ...... 514/314 |
| 6,060,488 A | | 5/2000 | Dodge et al. ............... 514/324 |
| 6,110,963 A | | 8/2000 | Malamas | |
| 6,162,930 A | * | 12/2000 | Pinney et al. ................. 549/57 |
| 6,166,069 A | | 12/2000 | Malamas et al. | |

FOREIGN PATENT DOCUMENTS

| | | |
|---|---|---|
| EP | 1028110 A1 | 8/2000 |
| WO | 00/48606 | 8/2000 |
| WO | 01/92224 A1 | 12/2001 |

OTHER PUBLICATIONS

Iwasaki et al, "Novel selective PDE IV Inhibitors as Anti-asthmatic Agents", CA125:86377, 1996.*
Hamel, E. Antimitotic Natural Products and Their Interactions with Tubulin 1996 16,207 Medicinal Research Reviews.
Gerwick, et al Structure of Curacin A, a Novel Antimitotic, Antiproliferative, and Brine Shrimp Toxic Natural Product from the Marine Cyanobacterium 1994 59,1243 J. Org. Chem.
Lavielle, et al New Amino Phosphonic Acid Derivatives of Vinblastine: Chemistry and Antitumor Activity 1991 34,1998 J. Med. Chem.
Kingston, et al The Chemistry of Taxol, a Clinically Useful Anticancer Agent 1990 53,1 J. Nat. Prod.
Schiff, P.B. et al Promotion of Microtubule Assembly in Vitro by Taxol 1979 277,665 Nature.
Swindell, C.S. et al Biologically Active Taxol Analogs with Deleted A–ring Chain Substituents and Variable C–2' Configurations 1991 34,1176 J. Med. Chem.
Nakada, M., et al The First Total Synthesis of the Antitumor Macrolide Rhizoxin: Synthesis of the Key Building Blocks 1993 34,1035 Tetrhaedron Lett.
Boger, D.L., et al Synthesis of the Lower Subunit of Rhizoxin 1992 75,2235 J. Org. Chem.
Kobayashi, S., et al Synthetic Study on an Antitumor Antibiotic Rhizoxin by Using an Enzymatic Process on Prochiral beta–Substituted Glutarates 1992 64,1121 Pure Appl. chem.
Rao, et al Studies Directed Towards the Total Synthesis of Rhizoxin: Stereoselective Synthesis of C–12 to C–18 Segment 1993 34,707 Tetrahedron Lett.
Lin, C.M., et al Antimitotic Natural Products Combretastatin A–4 and Combretastin A–2: Studies on the Mechanism of Their Inhibition of the Binding of Colchicine to Tubulin 1989 28,6984 Biochemistry.
Pettit, G.R., et al Antineoplastic agents, 122. Constituents of Combreturn caffrum 1987 50,386 J. Nat. Prod.
Dorr, R.T., et al Antitumor Activity of Combretastain A4 Phophate, a Natural Product Tubulin Inhibitor 1995 14, 131 Invest. New Drugs.
Hammonds, T.R. et al Studies To Show That With Podophyllotoxin the Early Replicative Stages of Herpes Simplex Virus Type 1 Depend Upon Functional Cytoplasmic Microtubules 1996 45,167 J. Med. Microbiol.

(List continued on next page.)

Primary Examiner—Deborah C. Lambkin
(74) Attorney, Agent, or Firm—Jackson Walker L.L.P.

(57) ABSTRACT

A diverse set of tubulin binding ligands have been discovered which are structurally characterized, in a general sense, by a semi-rigid molecular framework capable of maintaining aryl—aryl, pseudo pi stacking distances appropriate for molecular recognition of tubulin. In phenolic or amino form, these ligands may be further functionalized to prepare phosphate esters, phosphate salts, and phosphoramidates capable of demonstrating selective targeting and destruction of tumor cell vasculature.

16 Claims, 23 Drawing Sheets

OTHER PUBLICATIONS

Cortese, F. et al Podophyllotoxin as a Probe for the Colchicine Binding Site of Tubulin 1977 252,1134 J. Biol. Chem.

Nicolaou, K.C., et al Sythesis of Epothilones A and B in Solid and Solution Phase 1997 387, 268–272 Nature.

Pettit, G.R., et al Antineoplastic Agent 379. Synthesis of Phenstatin Phosphate 1998 41,168 8–1696 J. Med. Chem.

Jiang, J.B., et al Synthesis and Biological Evaluation of 2–Styrylquinazolin–4(3H)–ones, a New Class of Antimitotic Anticancer Agents Which Inhibit Tubulin Polymerization 1990 33,1721 J. Med. Chem.

Cushman, M., et al E. Synthesis and Evaluation of Stilbene and Dihydrostilbene Derivatives as Potential Anticancer Agents That Inhibit Tubulin Polymerization 1991 34,2579 J. Med. Chem.

Sawada, T., et al A Fluorescent Probe and a Photoaffinity Labeling Reagent to Study the Binding Site of Maytansinc and Rhizoxin on Tubulin 1993 4,284 Bioconjugate Cham.

Rao, S., et al Direct Photoaffinity Labeling of Tubulin with Taxol 1992 84,785 J. Natl. Cancer Insti.

Chavan, A.J., et al Forskolin Photoaffinity Probes for the Evaluation of Tubulin Binding Sites 1993 4,268 Bioconjugate Chem.

Sawada, T., et al Identification of the Fragment Photoaffinity–labeled with Azidodansyl–rhizoxin as Met–363–Lys–379 on beta–Tubulin, Biochem. 1993 45,1387 Biochem.

Staretz, M.E., et al Synthesis, Photochemical Reactions, and Tubulin Binding of Novel Photoaffinity Labeling Derivatives of Colchicine 1993 58,1589 J. Org. Chem.

Hahn, K.M., et al Synthesis and Evaluation of 2–Diazo–3, 3,3,–trifluoropropanoyl Derivatives of Colchicine and Podophyllotoxin as Photoaffinity Labels: Reactivity, Photochemistry, and Tubulin Binding, 1992 55,17 Photochem. Photobiol.

Sawada, T., et al Fluorescent and Photoaffinity Labeling Derivatives of Rhizoxin 1991 178,558 Biochem. Biophys. Res. Commun.

Wolff, J., et al Direct Photaffinity Labeling of Tubulin with Colchicine 1991 88,2820 Proc. Natl. Acad. Sci.

Floyd, L.J., et al Photoaffinity Labeling of Tubulin with (2–Nitro–4–azidophenyl) deacetylcolchicine: Direct Evidence for Two Colchicine Binding Sites 1989 28,8515 Biochemistry.

Safa, A.R., et al Photoaffinity Labeling of Tubulin Subunits with a Photoactive Analogue of Vinblastine 26,97 1987 Biochemistry.

Williams, R.F., et al A Photoaffinity Derivative of Colchicine: 6–(4'–Azido–2'–nitrophenylamino) hexanoyldeacetylcolchine. Photolabeling and Location of the Colchicine–binding Site on the alpha–subunit of Tubulin 260,137 94 1985 J. Biol. Chem.

Nogales, E., et al Structure of the a/B Tubulin Dimer by Electron Crystallography 391, 199–203 1998 Nature.

Shirai, R., et al Syntheses and Anti–Tubulin Activity of Aza–Combretastatins 699 1994 Biomedical Chem. Lett.

Grese, T.A., et al Structure–Activity Relationships of Selective Estrogen Receptor Modulators: Modifications to the 2–Arylbenzothiophene Core of Raloifene 40,146 1997 J. Med. Chem.

Palkowitz, A.D., et al Discovery and Synthesis of [6–Hydroxy–3–[4–[2–(1–piperidinyl)ethoxy]phenoxy]–2(4–hydroxyphenyl)]benzo[b]thiophene: A Novel, Highly Potent, Selective Estrogen Receptor Modulator 40, 1407 1997 J. Med. Chem.

Mullica, D.F., et al Characterization and Structural Analyses of Trimethoxy and Triethoxybenzo[b]thiophene 28, 289–295 1998 J. Chem. Cryst.

Pinney, K.G., et al A New Anti–Tubulin Agent Containing the Benzo[b]thiophene Ring System 143–2 1999 Bioorganic and Medicinal Chemistry Letters.

D'Amato, R.J., et al 2–Methoxyestradiol, an endogenous mamalian metabolite, inhibits tubulin polymerization by interacting at the colchine site 91, 3964 1994 Proc. Natl. Acad. Sci.

Cushman, M., et al Synthesis, Antintubulin and Antimitotic Activity, and Cytotoxicity of Analogs of 2–Methoxyestradiol, an Endogenous Mammalian Metobolite of Estradiol That Inhibits Tubulin Polymerization by Binding to the Colchicine Binding Site 38, 2041 1995 J. Med. Chem.

Hamel, E., et al Interactions of 2–Methoxyestradiol, and Endogenous Mammalian Metabolite, with Unpolymerized Tubulin and with Tubulin Polymers 35, 1304 1996 Biochemistry.

Boyd, M. R., et al Some Practical Considerations and Applications of the National Cancer Institute In Vitro Anticancer Drug Discovery Screen 34, 91 1995 Drug Development Research.

Dark, G.G., et al Combretastatin A–4, an Agent That Displays Potent and Selective Toxicity Toward Tumor Vasculature 57, 1829–1834 1997 Cancer Res.

Churcher, et al Synthesis of the Antimumor Agent Aglycon (+)–Calicheamicinone Using an 0–Quinone Monoketal Strategy 120, 10350 1998 J. American Chemical Society.

Clive, et al Synthesis of (+)–Calicheamicinone by Two Methods 120, 10332 1998 J. American Chemical Society.

Brown, et al Evolution of a Series of Peptidoleukotriene Antagonists: Synthesis and Struture–Activity Relationship of 1,6–Disubstituted Indoles and Indazoles 33, 1771–1781 1990 American Chemical Society.

Myers, et al A Convergent Synthetic Route to (+)–Dynemicin A and Analogs of Wide Structural Variability 119, 6072–6094 1997 J. American Chemical Society.

Rao, et al Radical Mediated Enantioselective Construction of C–1 to C–9 Segment of Rhizoxin 27, 3907–3910 1992 Tetrahedron Letters.

Zhang, et al Microtubule Effects of Welwistatin, a Cyanobacterial Indolinone that Circumvents Multiple Drug Resistance 49, 288–294 1996 Molecular.

Lavielle, et al New a–Amino Phosphonic Acid Derivatives of Vinblastine: Chemistry and Antitumor Activity 34, 1998–2003 1991 J. Med Chem.

Lingyun, et al Targeting The Tumor Vasculature With Combretastatin A–4 Disodium Phosphate: Effects on Radiation Therapy 242, 899–903 1998 Int. J. Radiation Oncology.

Pettit, et al Antineoplastic agent 389. New syntheses of the combretastatin A–4 prodrug 13 183–191 1998 Anti–Cancer Drug Design.

Bai, R., et al Characterization of the Interaction of Cryptophycin with Tubulin: Binding in the Vinca Domain, Competitive Inhibition of Dolastatin 10 Binding, and Unusual Aggegation Reaction 56, 4398–4406 1996 Cancer Res.

Monks, A., et al Feasibility of a High–Flux Anticancer Drug Screen Using a Diverse Panel of Cultured Human Tumor Cell Lines 83, 757–766 1991 J. Natl. Cancer Inst.

Flynn, B.E., et al A Novel Palladium–Mediated Coupling Approach to 2,3–Disubstituted Benzo[b]thiophenes and Its Application to the Synthesis of Tubulin Binding Agents 3, 651–654 2001 Organic Letters.

Pettit, G.R., et al Antineoplastic agents 429. Syntheses of the combretastatin A–1 and combretastatin B–1 prodrugs 15, 203–216 2000 Anti–Cancer Drug Design.

Tozer, et al Combretastatin A–4 Phosphate as Tumor Vascular–Targeting Agent: Early Effects in Tumors and Normal Tissues 59, 1626–1634 1999 Cancer Research.

Maxwell, et al Effects of Combretastatin on Murine Tumours Monitored by P MRS, $^1$H MRS and $^1$H MR1 42, 891–894 1998 J. Radiation Oncology.

Chaplin, et al Anti–Vascular Approaches to Solid Tumor Therapy: Evaluation of Combretastatin A4 Phosphate 19, 189–196 1999 Anticancer Research.

Beauregard, et al Magnetic resonance imaging and spectroscopy of combretastatin $A_4$ prodrug–induced disruption of tumour perfusion and energetic status 11, 1761–1767 1998 British Journal of Cancer.

Iyer, et al Induction of Apoptosis in Proliferating Human Endothelial Calls by the Tumor–specific Antiangiogenesis Agent Combretastatin A–4[1] 58, 4510–4514 1998 Cancer Research.

Jones, et al Antiestrogens. 2. Structure–Activity Studies in a Series of 3–Aroyl–2–arylbenzo[b]thiphene Derivatives leading to [6–Hydroxy–2(4–hydroxyphenyl)benzo[b]thien–3–y1][4–[2–(1–piperidinyl)ethoxy]–phenyl]methanone Hydrochloride (LY156758, a Remarkably Effective Estrogen Antagonist with Only Minimal Intrinsic Estrogenicity 27, 1057–1066 1984 J. Med Chem.

Pettit, et al Antineoplastic agents 393. Synthesis of the trans–isomer of combretastatin A–4 prodrug 13, 981–993 1998 Anti–Cancer Drug Design.

* cited by examiner

Benzo[b]thiophene (1)

Benzo[b]thiophene Phenol (2)

Benzo[b]thiophene Prodrug (3)

CA-4

CA-4P

Benzoyl-Dihydronaphthalene (13)

Aryl-Dihydronaphthalene (14B)

Amino-Dihydronaphthalene (15)

Dihydronaphthalene Phosphoramidate Prodrug (16)

Nafoxidene

18. $R^1 = OCH_3$, $R^2 = H$
19. $R^1 = H$, $R^2 = OCH_3$

20. $R^1 = OCH_3$, $R^2 = H$
21. $R^1 = H$, $R^2 = OCH_3$

22. $R^1 = OCH_3$, $R^2 = H$, $R^3 = H$
23. $R^1 = H$, $R^2 = OCH_3$, $R^3 = H$
24. $R^1 = H$, $R^2 = H$, $R^3 = OCH_3$
25. $R^1 = OCH_3$, $R^2 = OCH_3$, $R^3 = H$

26. $R^1 = OCH_3$, $R^2 = H$, $R^3 = H$
27. $R^1 = H$, $R^2 = OCH_3$, $R^3 = H$
28. $R^1 = H$, $R^2 = H$, $R^3 = OCH_3$
29. $R^1 = OCH_3$, $R^2 = OCH_3$, $R^3 = H$

BFP-disodium salt

Benzoyl-Dihydronaphthalene (13)

R = alkyl, branched alkyl, etc.

R = alkyl, branched alkyl, etc.

Previously Described by Pinney and Co-Workers

BFP-disodium salt

R = alkyl, branched alkyl, etc.

R = alkyl, branched alkyl, etc.

Enediyne Ligand 30

R = alkyl, branched alkyl, etc.

R = alkyl, branched alkyl, etc.

C-5- DHN-P

C-7- DHN-P 2,3-Diarylbenzo[*b*]thiophene Prodrug 2,3-Diarylbenzo[b]thiophene Prodrug

CA-1P

US 6,593,374 B2

TUBULIN BINDING LIGANDS AND CORRESPONDING PRODRUG CONSTRUCTS

CROSS-REFERENCE TO RELATED APPLICATIONS

Priority is claimed from provisional application U.S. Ser. No. 60/188,295 filed on Mar. 10, 2000, and incorporated by reference herein. Attention is called to U.S. Pat. No. 6,162,930 issued to Pinney et al. on Dec. 19, 2000, which is incorporated in its entirety by reference herein.

BACKGROUND

Tubulin is currently among the most attractive therapeutic targets in new drug design for the treatment of solid tumors. The heralded success of vincristine and taxol along with the promise of combretastatin A-4 (CSA-4) prodrug and dolastatin 10, to name just a few, have firmly established the clinical efficacy of these antimitotic agents for cancer treatment.

An aggressive chemotherapeutic strategy toward the treatment and maintenance of solid-tumor cancers continues to rely on the development of architecturally new and biologically more potent anti-tumor, anti-mitotic agents which mediate their effect through a direct binding interaction with tubulin. A variety of clinically-promising compounds which demonstrate potent cytotoxicity and antitumor activity are known to effect their primary mode of action through an efficient inhibition of tubulin polymerization.[1] This class of compounds undergoes an initial interaction (binding) to the ubiquitous protein tubulin which in turn arrests the ability of tubulin to polymerize into microtubules which are essential components for cell maintenance and division.[2] During metaphase of the cell cycle, the nuclear membrane has broken down and the cytoskeletal protein tubulin is able to form centrosomes (also called microtubule organizing centers) and through polymerization and depolymerization of tubulin the dividing chromosomes are separated. Currently, the most recognized and clinically useful members of this class of antimitotic, antitumor agents are vinblastine and vincristine[3] along with taxol.[4] Additionally, the natural products rhizoxin,[5] combretastatin A-4 and A-2,[6] curacin A,[1] podophyllotoxin,[7] epothilones A and B,[8] dolastatin 10[9] and welwistatin[10] (to name just a few) as well as certain synthetic analogues including phenstatin,[11] the 2-styrylquinazolin-4(3H)-ones (SQO),[12] and highly oxygenated derivatives of cis- and trans-stilbene[13] and dihydrostilbene are all known to mediate their cytotoxic activity through a binding interaction with tubulin. The exact nature of this binding site interaction remains largely unknown, and definitely varies between the series of compounds. Photoaffinity labeling and other binding site elucidation techniques have identified several key binding sites on tubulin: colchicine site, vinca alkaloid site, and a site on the polymerized microtubule to which taxol binds.[1a,14]

An important aspect of this work requires a detailed understanding, on the molecular level, of the "small molecule" binding domain of both the α and β subunits of tubulin. The tertiary structure of the α,β tubulin heterodimer was reported in 1998 by Downing and co-workers at a resolution of 3.7 Å using a technique known as electron crystallography.[15] This brilliant accomplishment culminates decades of work directed toward the elucidation of this structure and should facilitate the identification of small molecule binding sites, such as the colchicine site, through techniques such as photoaffinity and chemical affinity labeling.

BRIEF DESCRIPTION OF THE INVENTION

We have developed a working hypothesis suggesting that the discovery of new antimitotic agents may result from the judicious combination of a molecular template (scaffold) which in appropriately substituted form (ie. phenolic moieties, etc.) interacts with estrogen receptor (ER), suitably modified with structural features deemed imperative for tubulin binding (arylalkoxy groups, certain halogen substitutions, etc.). The methoxy aryl functionality seems especially important for increased interaction at the colchicine binding site in certain analogs.[16] Upon formulation of this hypothesis concerning ER molecular templates, our initial design and synthesis efforts centered on benzo[b]thiophene ligands modeled after raloxifene, the selective estrogen receptor modulator (SERM) developed by Eli Lilly and Co.[17] Our initial studies resulted in the preparation of a very active benzo[b]thiophene-based antitubulin agent.[18-21] In further support of our hypothesis, recent studies have shown that certain estrogen receptor (ER) binding compounds as structurally modified estradiol congeners (2-methoxyestradiol, for example) interact with tubulin and inhibit tubulin polymerization.[22] Estradiol is, of course, perhaps the most important estrogen in humans, and it is intriguing and instructive that the addition of the methoxy aryl motif to this compound makes it interactive with tubulin. It is also noteworthy that 2-methoxyestradiol is a natural mammalian metabolite of estradiol and may play a cell growth regulatory role especially prominent during pregnancy. The term "phenolic moiety" means herein a hydroxy group when it refers to an R group on an aryl ring.

DETAILED DESCRIPTION OF THE INVENTION

Figure 1:
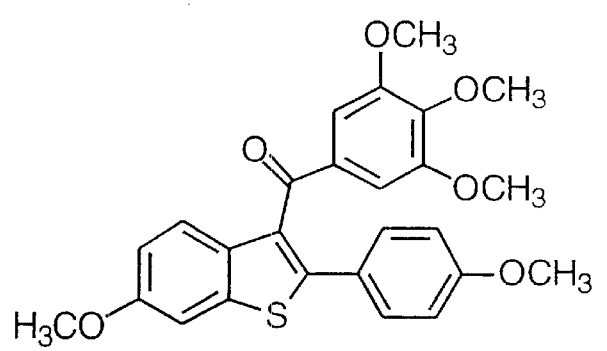
FIG. 1 shows benzo[b]thiophene ligands and prodrug construct.
Figure 1:
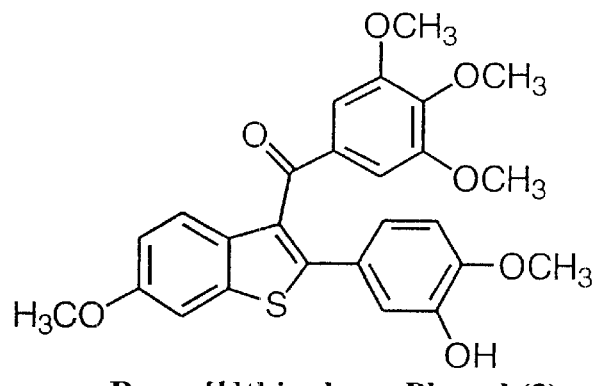
Figure 1:
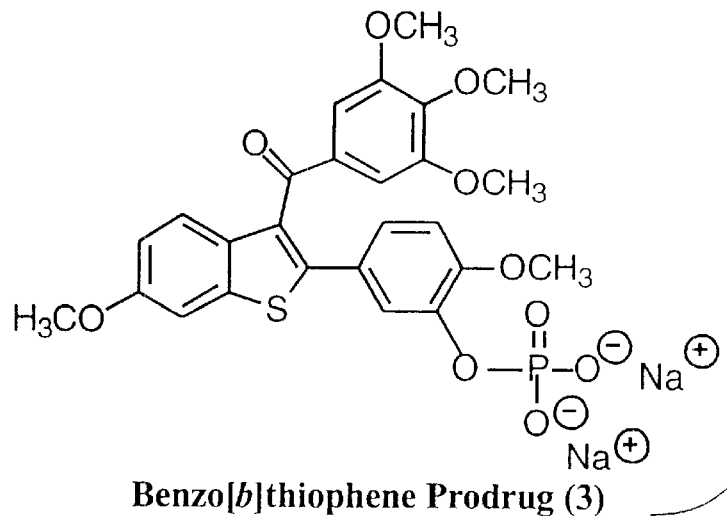

The design premise that molecular skeletons of traditional estrogen recepter (ER) binding compounds can be modified with structural motifs reminiscent of colchicine and combretastatin A-4 to produce inhibitors of tubulin polymerization has been validated by the benzo[b]thiophene and benzo[b]furan classes of new antimitotic agents.[18-21] The lead compounds in each series (FIGS. 1 and 10), demonstrate remarkable biological activity against a variety of human cancer cell lines. For example, the 3,4,5-trimethoxybenzo[b]thiophene (ligand 1, FIG. 1) demonstrates potent cytotoxicity and inhibition of tubulin polymerization. In the NCI 60 cell line panel,[23] this compound produces a mean panel $GI_{50}=2.63 \times 10^{-7}$ M. In addition, we have recently prepared an indole ligand that is among the most potent (including both natural and synthetic) of all compounds currently known to bind to the colchicine site on β-tubulin ($GI_{50}=5.1 \times 10^{-9}$ M (cytotoxicity against human cancer cells), and $IC_{50}=0.5–1.0$ μM (inhibition of tubulin polymerization)).[24]

Further significance is given to new drugs that bind to the colchicine site since it has recently been shown that combretastatin A-4 also demonstrates anti-angiogenesis activity.[25] An emerging area of cancer chemotherapy centers on the development of anti-angiogenesis drugs which selectively target the vasculature of tumor cells while leaving healthy cells intact. Combretastatin A-4 prodrug is one of the leading new candidates from among a relatively small collection of known world compounds which display this anti-angiogenic efficacy. Discovered by Professor George R. Pettit (Arizona State University) from a willow tree (*combretum caffrum*) in South Africa in the 1970s, this compound is currently undergoing phase I clinical evaluation sponsored and licensed by OXiGENE, Inc.

Combretastatin A-4 (CSA-4) is a potent inhibitor of tubulin polymerization which binds to the colchicine site on β-tubulin. Interestingly, CSA-4 itself does not demonstrate destruction of tumor vasculature, while CSA-4 prodrug is very active in terms of tumor vasculature destruction.[26] It is very likely that the phosphate ester portion of the prodrug undergoes dephosphorylation (perhaps through the action of endothelial alkaline phosphatases) selectively at sites of enhanced vascularization to reveal the potent CSA-4 itself which destroys the tumor cell through an inhibition of tubulin polymerization. The dephosphorylation event takes place selectively at tumor cells since tumor cells represent sites of prolific vascularization. This need for enhanced vascularization is not necessary for healthy cells. Hence, this dual-mode reactivity profile is clearly important in order to target tumor cells selectively over healthy cells. This is a proposal which has been advanced by Professor Ronald Pero (OXiGENE, Inc., University of Lund) for which a variety of strong evidence has been obtained.

Figure 1B:
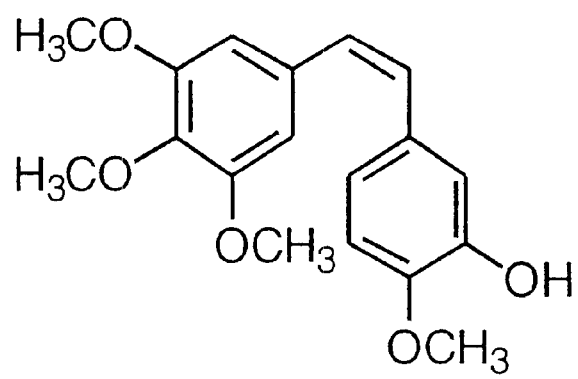
FIG. 1B shows the compound structures combrestatin-4A (CA-4) and combrestatin-4A prodrug (CA-4P).
Figure 1B:
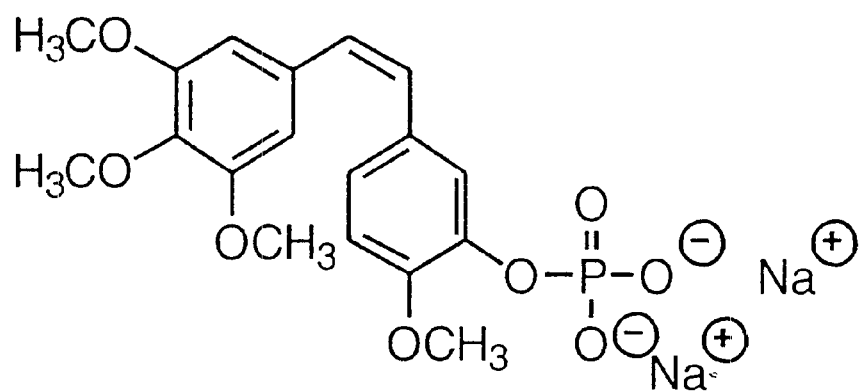

The possibility clearly exists that some of the new prodrug ligands described herein, which are structurally related to combretastatin A-4 (see FIG. 1B), may also function through additional biological mechanisms involving both anti-angiogenic activity, and the selective targeting and destruction of tumor cell vasculature. Clearly the ability to selectivity disrupt the blood-flow to developing tumor cells is a potential breakthrough in the ever up-hill battle against cancer.

Synthesis of a Benzo[b]thiophene Based Prodrug

Bioavailability is a major problem for many compounds that show good in vitro activity in order to develop them as anti-cancer agents. The efficacy of a drug depends on many factors, and one of the important factors is the water solubility of the drug since the human body contains 90% water. The mode of administration of many anti-cancer agents is often as an intravenous injection. Safe and efficient pharmaceutical formulations are imperative for the success of any drug. Although CSA-4 has demonstrated unique biological activity as an anti-cancer agent, poor water solubility proved a significant hurdle to overcome for its development as a cancer treatment agent. There have been many reports on the synthesis of water soluble prodrug formulations of CSA-4. Of all these, the disodium phosphate salt prepared by Pettit and co-workers[26] has proved to be most attractive, and this analog is currently undergoing phase I clinical trials sponsored by Oxigene Inc.

Figure 2:
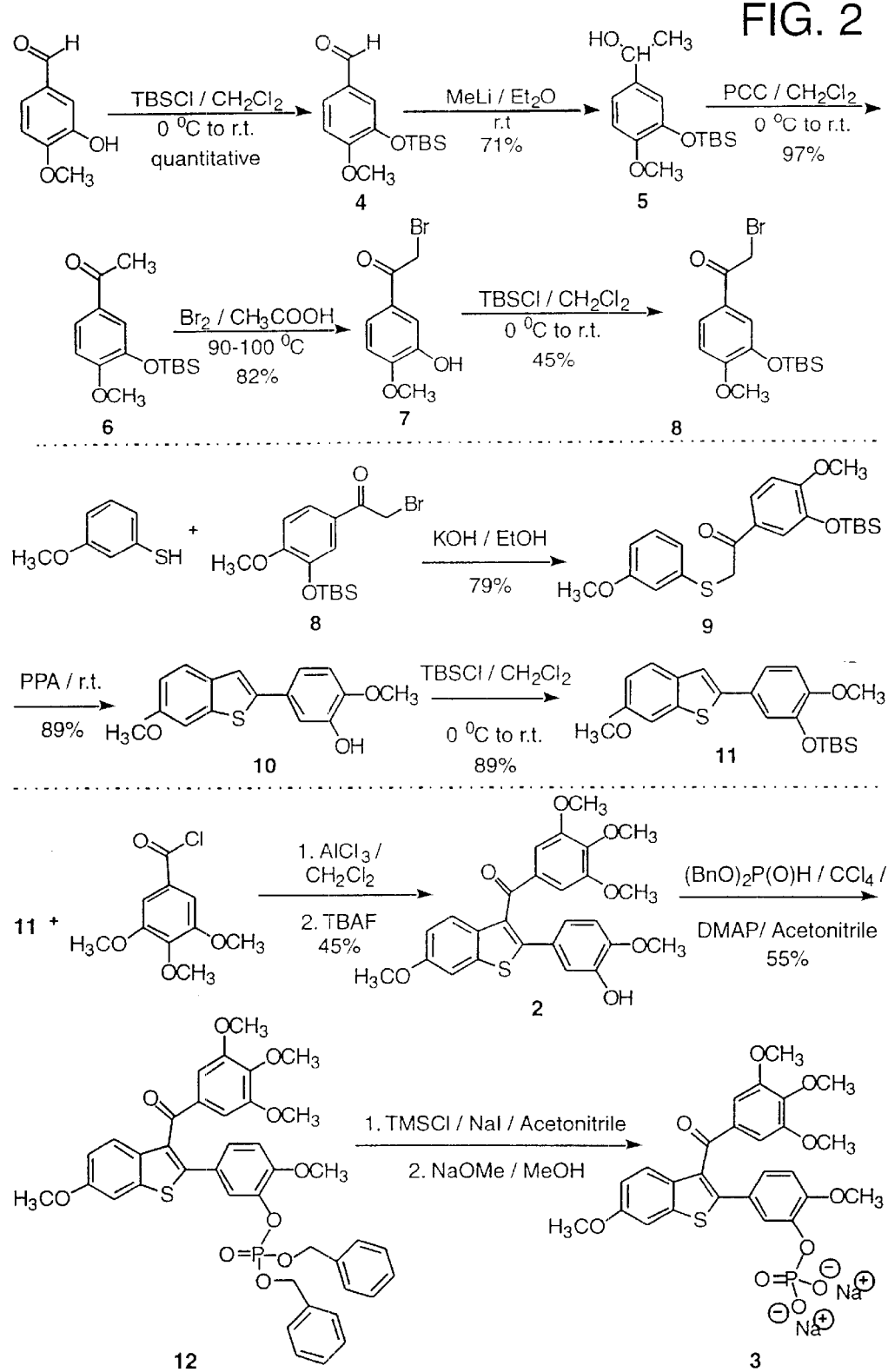
FIG. 2 shows synthesis of benzo[b]thiophene prodrug construct.

Excellent in vitro cytotoxicity shown by the lead compound 1 (FIG. 1) in our benzo[b]thiophene series, has prompted us to design a prodrug for this lead compound. Since 2-bromo-(2'-hydroxy-4'-methoxy)-acetophenone is not commercially available, we synthesized the compound from 4-methoxy-2-hydroxybenzaldehyde (isovanillin). Protection of isovanillin with tert-butyldimethylsilyl chloride (TBSC1) gave compound 4 (FIG. 2). Methylation of 4 with methyl lithium (MeLi) yielded alcohol 5. PCC oxidation of this alcohol followed by bromination with liquid bromine in acetic acid at 100° C. resulted in hydroxy deprotected bromoacetophenone 7. The hydroxy group was re-protected with TBSCl to give compound 8. Treatment of 8 with 3-methoxybenzene thiol gave sulfide 9, which on cyclization with PPA afforded para cyclized thiophene 10 in good yield. Since the PPA step also caused deprotection of the silyl protected alcohol, the hydroxy group was re-protected as its corresponding silyl ether by treatment with TBSCl to give compound 11 (FIG. 2). Friedel-Craft's acylation of 11 with 3,4,5-trimethoxybenzoyl chloride gave the hydroxyprotectedbenzo[b]thiophene analog along with some deprotected product. The reaction with 3-methoxybenzene thiol resulted in isolation of a small amount of hydroxy deprotected sulfide as well. The acylated product, on deprotection with tert-butylammonium fluoride, resulted in formation of hydroxythiophene ligand 2. Phosphorylation of this phenol with dibenzylphosphite afforded dibenzylphosphate 12. Deprotection of the benzyl groups with chlorotrimethyl silane (TMSCl) and sodium iodide followed by treatment with sodium methoxide in methanol afforded the disodium phosphate prodrug 3 (FIG. 2) of the lead benzo[b]thiophene ligand 1.

Following a very similar methodology, one skilled in the art can readily prepare a wide variety of prodrug constructs containing other metals salts, alkyl groups, or nitrogen based phosphoramidates and their corresponding metal salts.

Figure 2B:
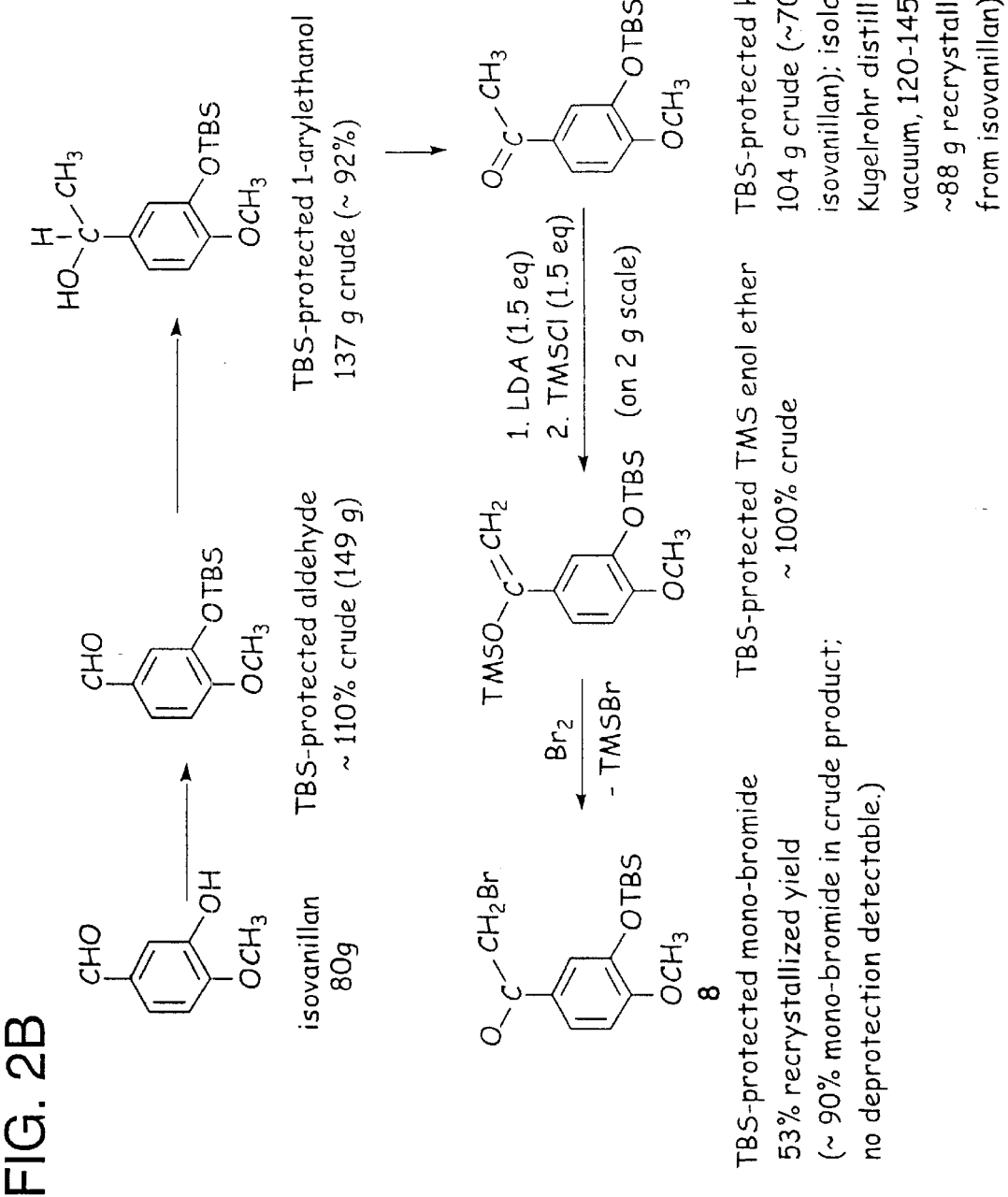
FIG. 2B shows new methodology for the formation of key bromide intermediate.

We have recently developed (see FIG. 2B) an important improvement in the synthesis of the benzo[b]thiophene prodrug (3) which involves a new methodology for the formation of the key bromide intermediate (8). This method involves conversion of the ketone moiety to a silyl enol ether followed by treatment with bromine to afford bromide 8 in high yield and purity. This methodology is a tremendous improvement over the methodology illustrated in FIG. 2 since it allows facile scale-up of bromide 8 without chromatography. Bromide 8 is a key intermediate in the synthesis of vascular targeting agents which incorporate benzo[b]thiophene, indole, and benzofuran molecular skeletons and hence the new methodology for the formation of bromide 8 is especially noteworthy.

Synthesis of a Dihydronaphthalene-based Prodrug

We have previously prepared a benzoyl substituted dihydronaphthalene-based antimitotic agent 13 (FIG. 3) which demonstrates strong cytotoxicity and excellent inhibition of tubulin polymerization.[19] Our interest in preparing the aryl substituted dihydronaphthalene ligand 14B was based on our molecular recognition studies which suggest an optimal aryl—aryl distance (centroid to centroid) for enhanced tubulin binding.

Figure 4:
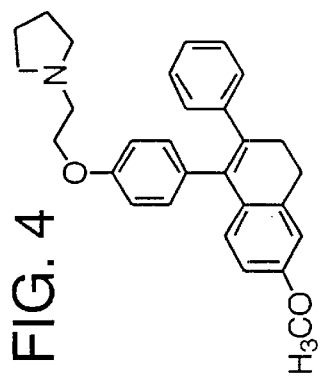
FIG. 4 shows compound structure nafoxidene.
Figure 5:
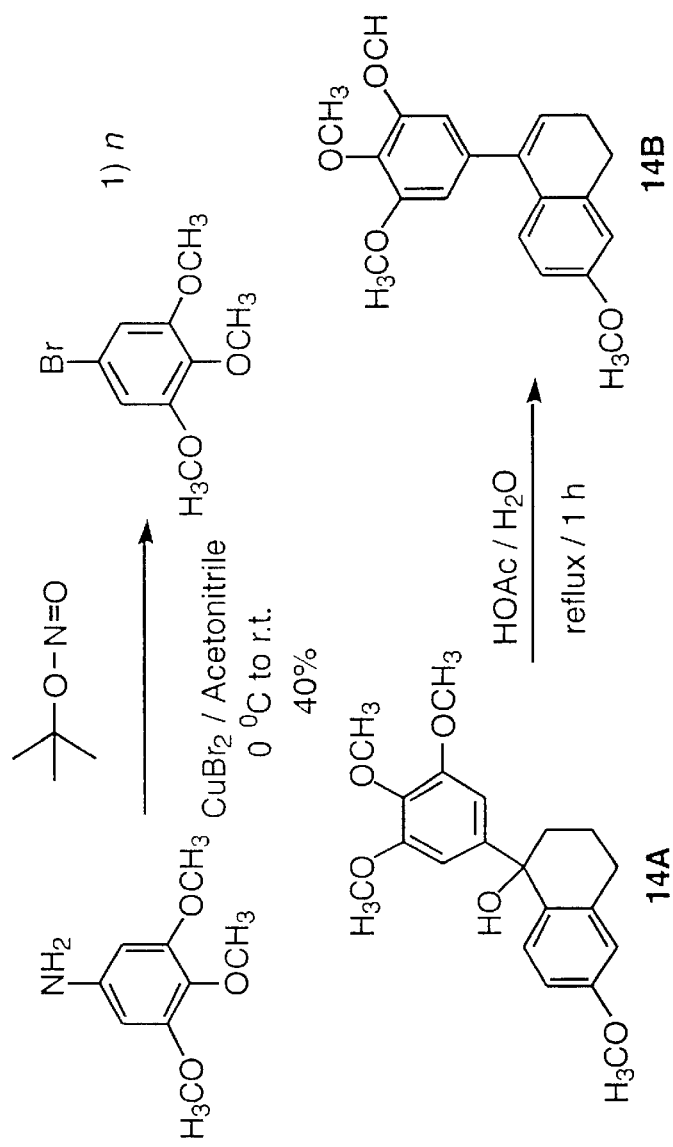
FIG. 5 shows synthesis of a dihydronaphthalene antitubulin ligand.

The dihydronaphthalene derivative 14B, which mimics the ER binding ligand nafoxidene (FIG. 4), was prepared as described in FIG. 5. 3,4,5-Trimethoxy-1-bromobenzene was obtained via a Sandmeyer reaction by treatment of the corresponding trimethoxy aniline with copper bromide and tert-butyl nitrite. The bromobenzene was subjected to lithium-halogen exchange with n-BuLi followed by reaction with 6-methoxy-1-tetralone to afford the dehydrated dihydronaphthalene derivative 14B (FIG. 6).

Figure 6:
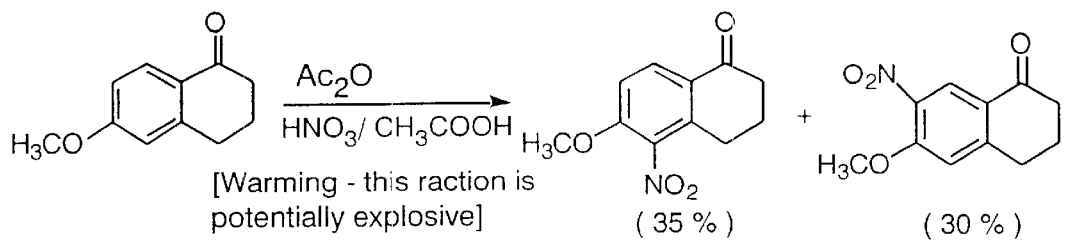
FIG. 6 shows synthesis of a dihydronaphthalene phosphoramidate prodrug.
Figure 6:
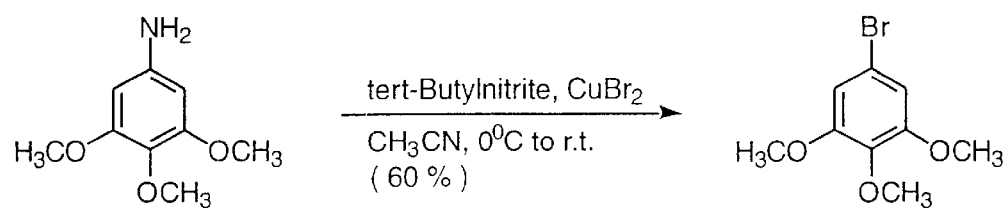
Figure 6:
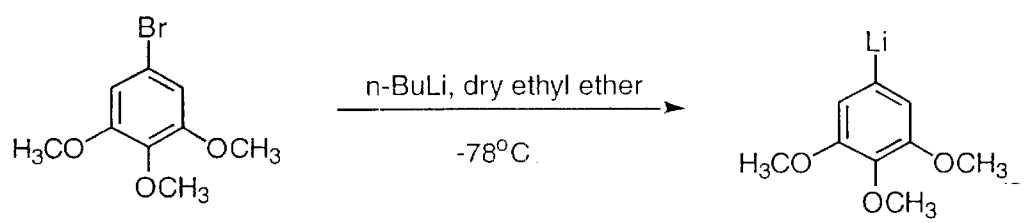
Figure 6:
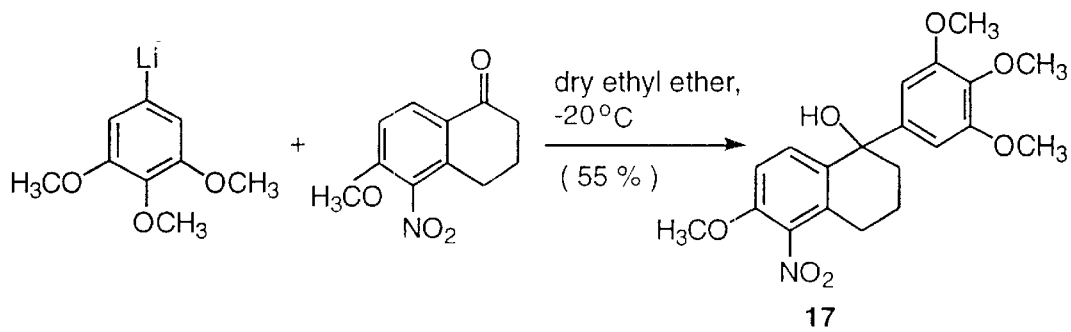
Figure 6:
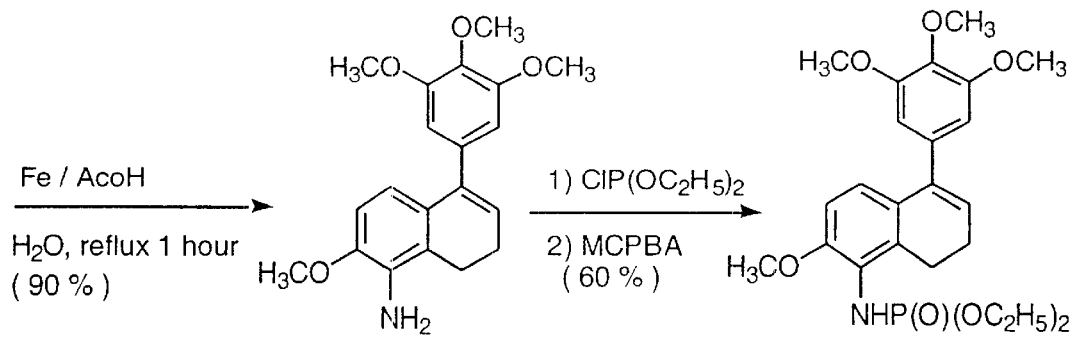

The amino derivative 15 and the phosphoramidate prodrug 16 are obvious extensions of this work (FIG. 6). The phosphoramidate choice was derived from our previous studies of combretastatin-based phosphoramidates.[24] These phosphoramidates appear to display the same type of selectivity for tumor vasculature as their phosphate salt counterparts.[27]

Figure 7:
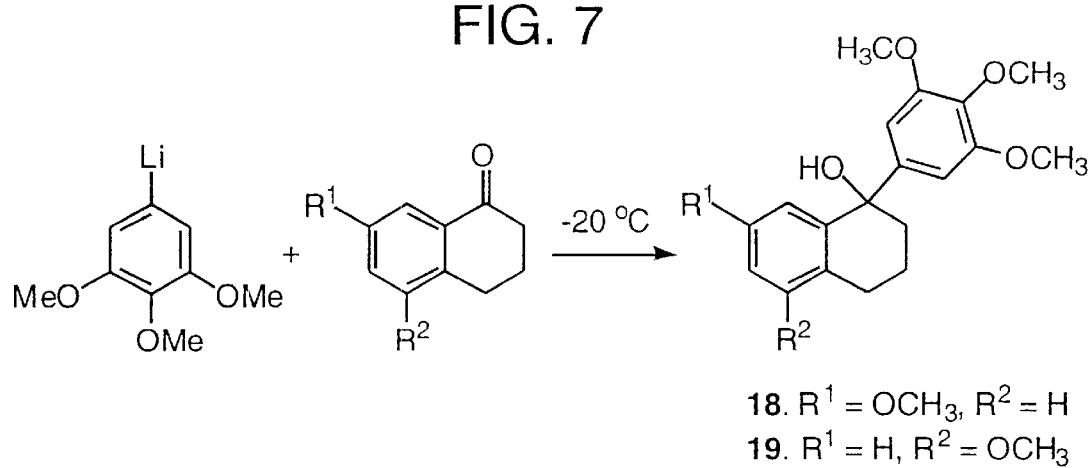
FIG. 7 shows a general synthetic route for the preparation of dihyronaphthalenes.
Figure 7:
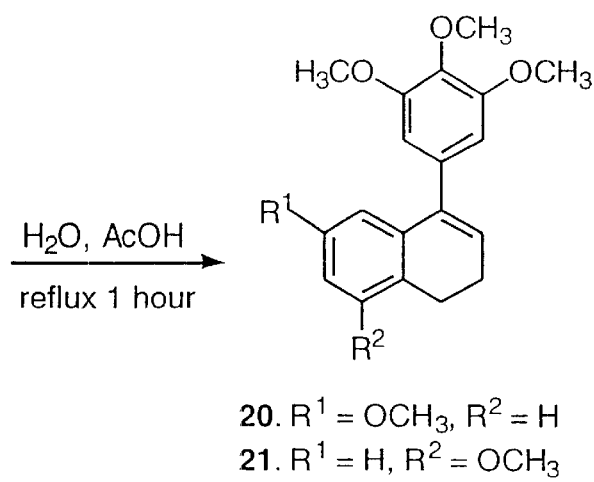

In a synthetic manner similar to that illustrated in FIG. 6, a variety of other dihydronaphthalene derivatives may readily be synthesized (FIG. 7). In addition to these C-5 functionalized derivatives, it should prove facile to prepare the phosphate disodium salt, phosphate ester, and phosphoramidate at the C-7 position of the dihyronaphthalene ring system through a synthetic route reminiscent of that delineated in FIG. 6.

Figure 8:
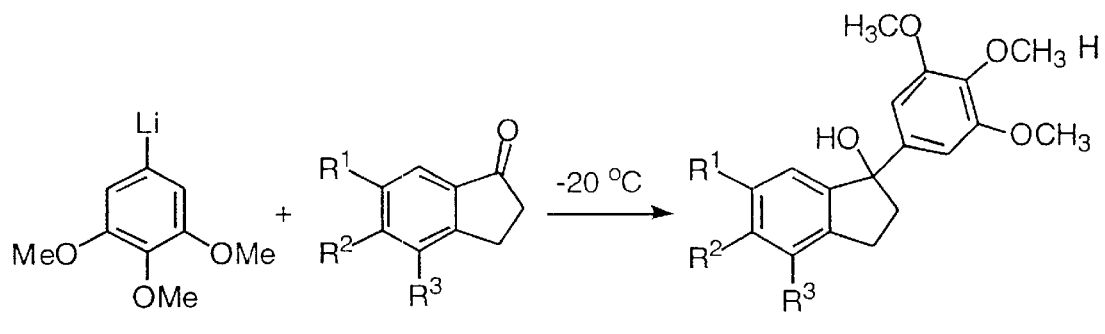
FIG. 8 shows preparation of indene analogs.
Figure 8:
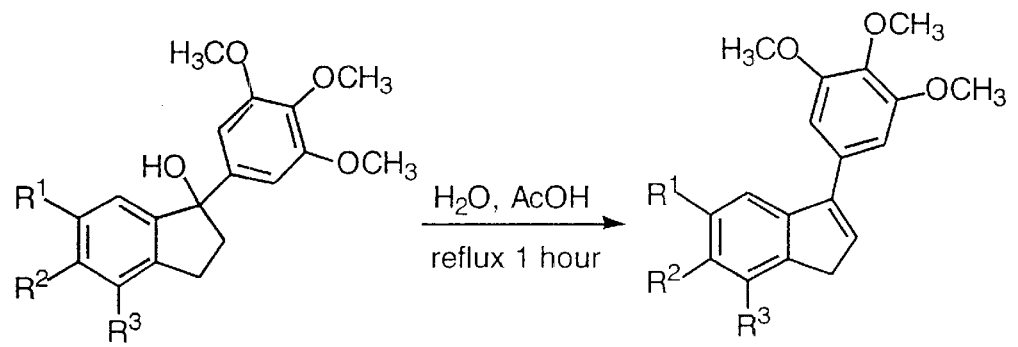

Due in part to the strong biological activity demonstrated by certain of the dihydronaphthalene ligands, we have also prepared a variety of indene derivatives by an essentially analogous synthetic route (FIG. 7). It will be an obvious extension for anyone skilled in the art to adapt the synthetic strategy showcased in FIGS. 6, 7, and 8 in order to facilitate the preparation of phenolic and amino analogs which can be readily transformed into the corresponding phosphate salts and phosphoramidates respectively (FIGS. 8B and 8C).

Figure 9:
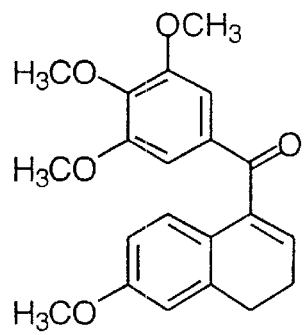
FIG. 9 shows prodrug constructs of benzoyl-dihyronaphthalene.
Figure 9:
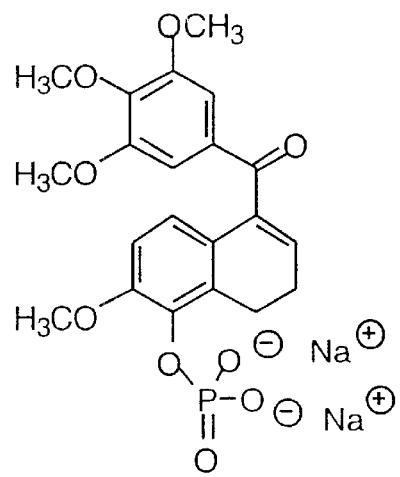
Figure 9:
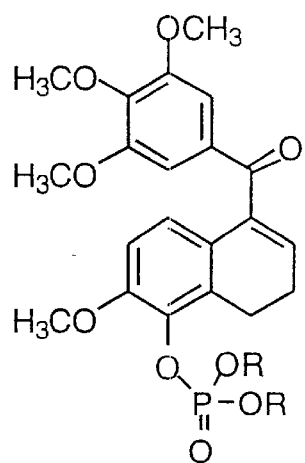
Figure 9:
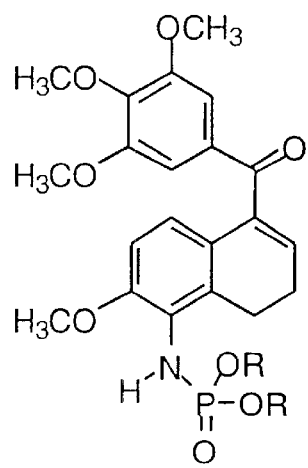

The benzoyldihydronaphthalene derivative 13 has been previously described by Pinney and co-workers.[19] Based on the other prodrug constructs described herein, the preparation of phosphate esters, salts, and phosphoramidates based on ligand 13 should be obvious to anyone skilled in the art (FIG. 9). It is important to note that the substitution patterns of phosphate and phosphoramidate shown in FIG. 9 at the C-5 position of the dihydronaphthalene can alternatively be contained at the C-7 position.

Synthesis of a Benzofuran Based Prodrug

Figure 8B:
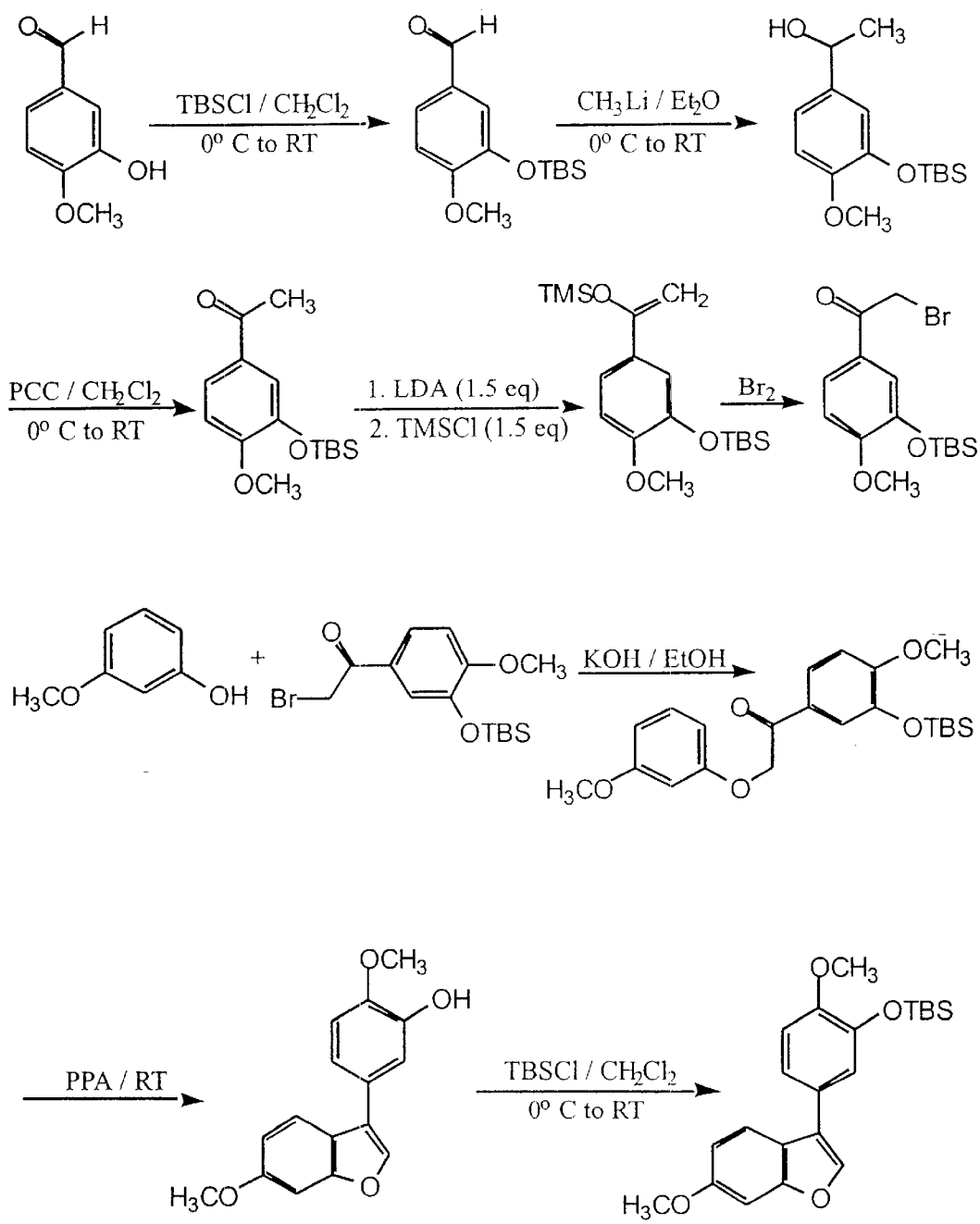
FIG. 8B shows synthesis of BFP-disodium salt.
Figure 8C:
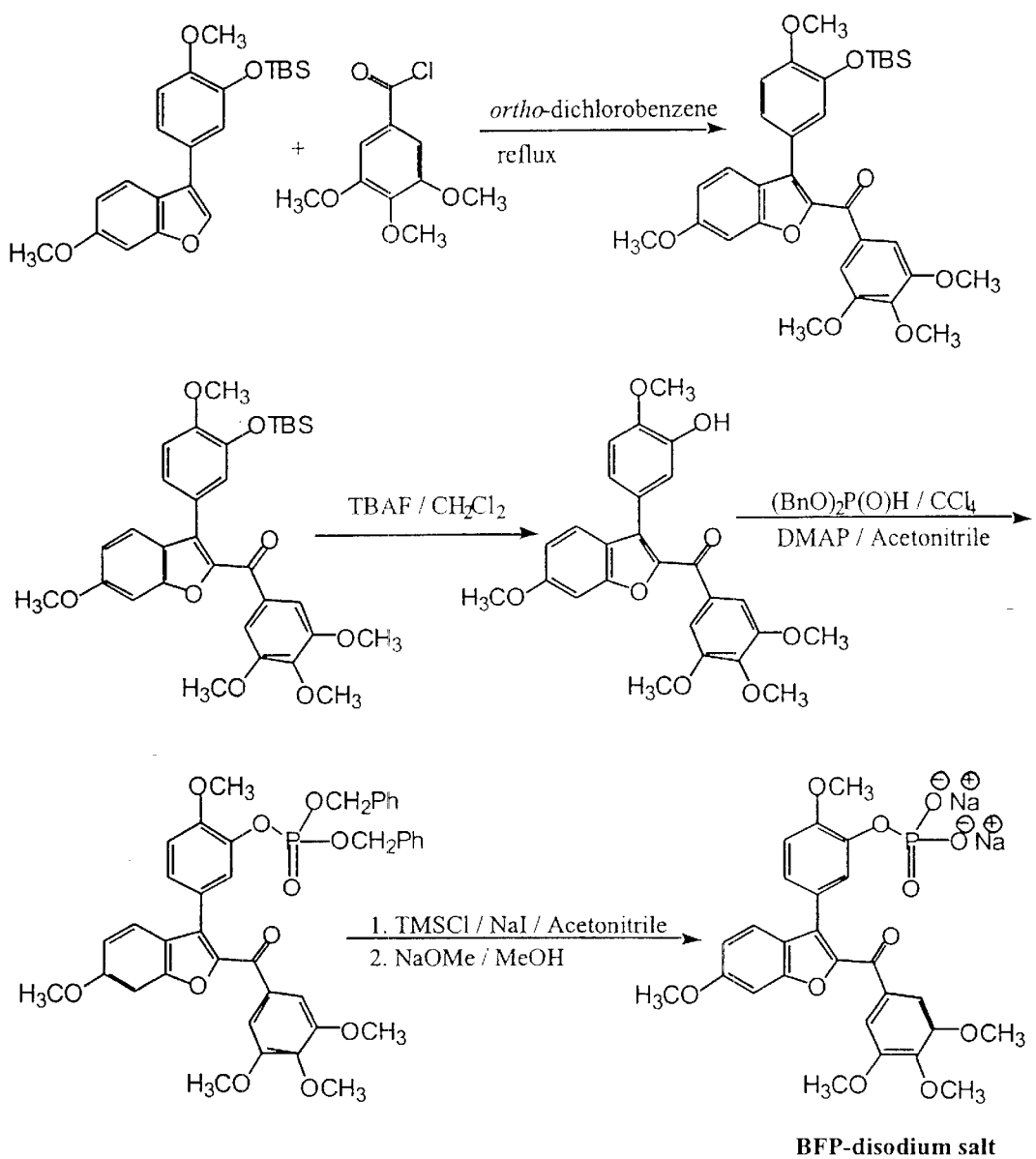
FIG. 8C continues to show synthesis of BFP-disodium salt.
Figure 10:
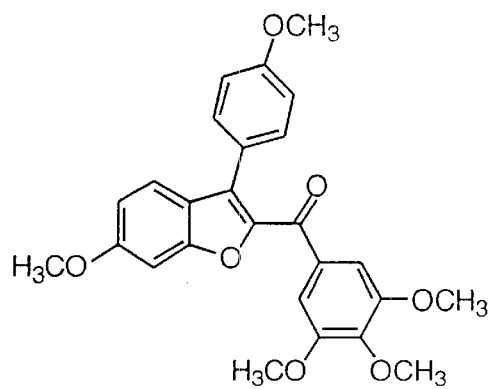
FIG. 10 shows prodrug constructs of benzofurans.
Figure 10:
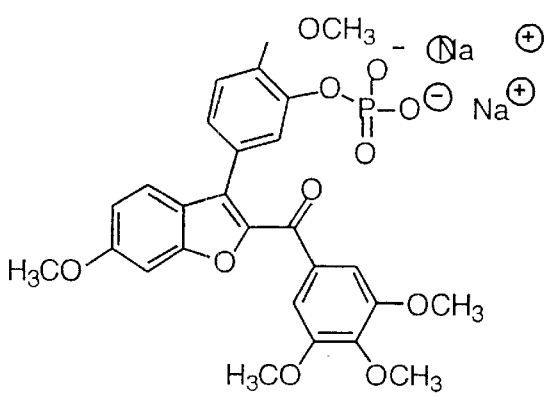
Figure 10:
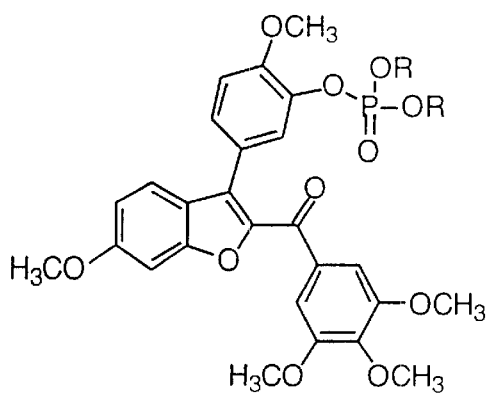
Figure 10:
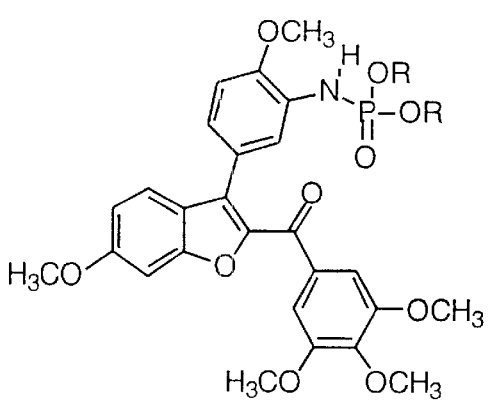

A variety of benzofuran derivatives have been previously described by Pinney and co-workers.[19] Based on the other prodrug constructs described herein, the preparation of phosphate esters, salts, and phosphoramidates based on the benzofuran ring skeleton should be obvious to anyone skilled in the art (see FIGS. 8B, 8C and 10). It is important to note that the substitution patterns of phosphate and phosphoramidate shown in FIG. 9 at the C-3 position on the pendant aryling of the dihydronaphthalene can alternatively be contained at the C-7 position. It is important to note that the substitution patterns of phosphate and phosphoramidate shown in FIG. 10 at the C-3' position on the pendant aryl ring of the benzofuran can alternatively be contained at other aryl positions, most notably C-5 and C-7.

Synthesis of an Enediyne Based Prodrug

Figure 11:
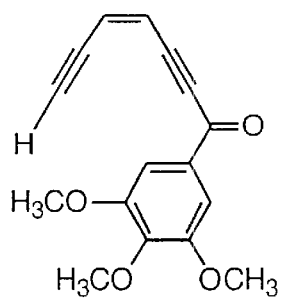
FIG. 11 shows prodrug constructs of enediyne combretastatin mimics.
Figure 11:
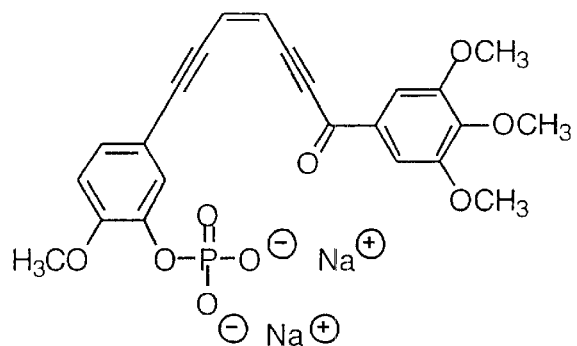
Figure 11:
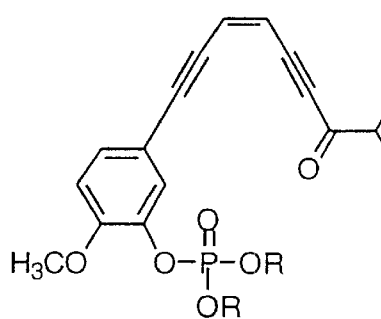
Figure 11:
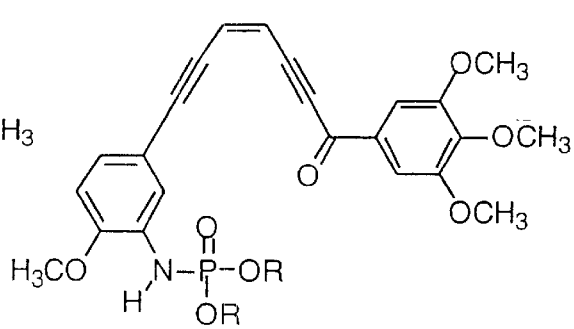

We have recently prepared an enediyne based compound 30 (FIG. 11) in which one aryl ring mimics the trimethoxy aryl ring of combretastatin A-4, while a triple bond moiety functions as a pi bond rich mimic of the second aryl ring of combretastatin A-4. Since this compound demonstrates strong cytotoxicity and excellent inhibition of tubulin polymerization, a natural extension is the preparation of phosphate ester derivatives, disodium phosphate salts, and phosphoramidates following the synthetic protocols established in this application. A further extension of this work will be the preparation of analogous enediyne prodrug constructs which do not contain the carbonyl group at either terminus of the enediyne bridge (diaryl enediyne constructs) and compounds which contain a carbonyl group at both termini of the endiyne bridge connecting the bridge to an appropriately substituted aryl ring.

Figure 12:
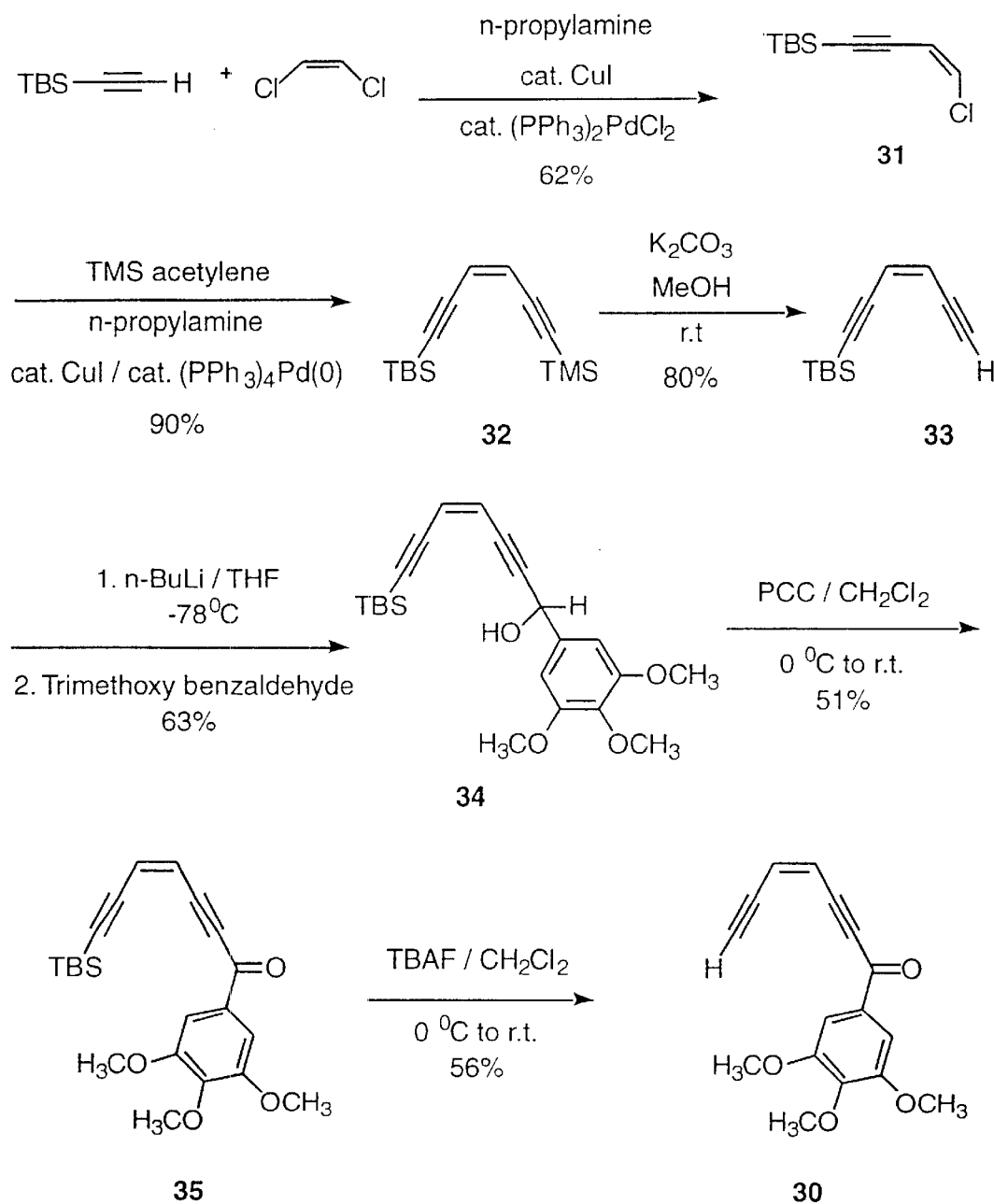
FIG. 12 shows preparation of enediyne ligand 30.

Andrew Myers and co-workers along with several other groups have reported the synthesis of cis-enediynes that are utilized for the total synthesis of dynemicin and calicheamicin.[28] We have utilized a similar synthetic route to prepare modified cis-enediynes, to incorporate the structural features of CA-4, as tubulin binding ligands. The cis-enediynes are prepared by coupling TBS-acetylene to cis-1,2-dichloroethylene in the presence of dichloro-bis-triphenylphosphine palladium (II) catalyst, CuI, and n-propylamine to yield eneyne 31 (FIG. 12). A second coupling reaction of eneyne 31 with TMS-acetylene in the presence of tetrakis-triphenylphosphine palladium (0) and CuI functioning as catalysts, and n-propylamine, an acid quenching base, resulted in enediyne 32 which is protected on both ends by TBS and TMS groups which can be preferentially deprotected. Deprotection of the TMS group with $K_2CO_3$ in methanol afforded compound 33, which upon lithiation with n-BuLi in THF followed by reaction with 3,4,5-trimethoxybenzaldehyde resulted in the formation of alcohol 34. PCC oxidation of alcohol 34 followed by deprotection of the TBS group with TBAF gave the trimethoxybenzoyl-substituted enediyne 30 (FIG. 12).

Synthesis of a Benzo[b]thiophene Aryloxy Ether Prodrug

Figure 13:
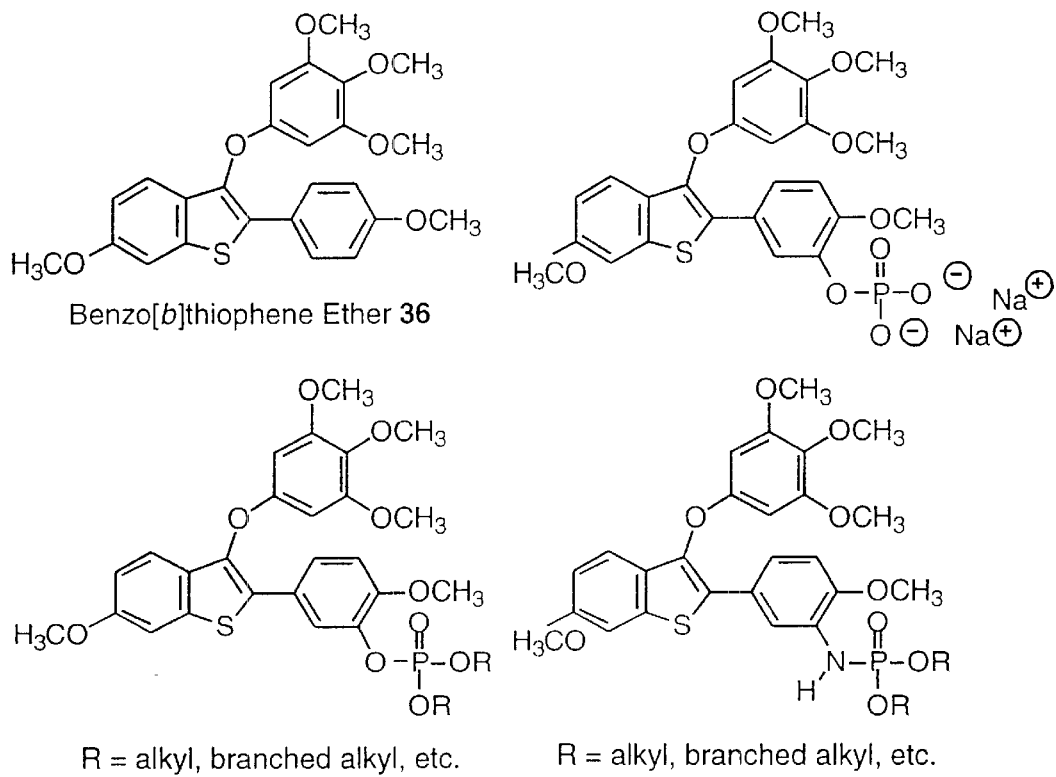
FIG. 13 shows prodrug constructs of benzo[b]thiophene aryl ether derivatives.

We have previously described a benzo[b]thiophene aryloxy ether based compound 36 (FIG. 13) in which the carbonyl group has been replaced with an oxygen atom[19]. Since this compound demonstrates strong cytotoxicity and excellent inhibition of tubulin polymerization, a natural extension is the preparation of phosphate ester derivatives, disodium phosphate salts, and phosphoramidates following the synthetic protocols established in this application.

Synthesis of a Hydroxy-dihydronaphthalene Analog

Figure 3:
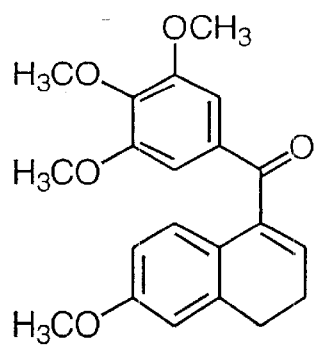
FIG. 3 shows dihydronaphthalene ligands and prodrug construct.
Figure 3:
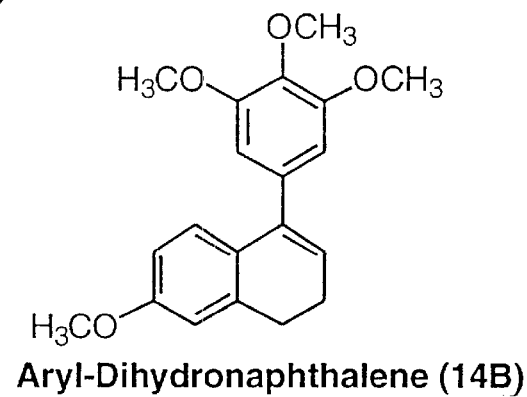
Figure 3:
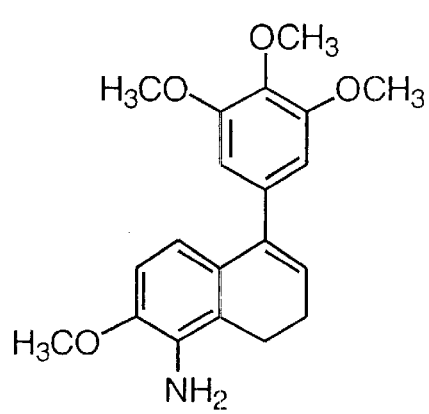
Figure 3:
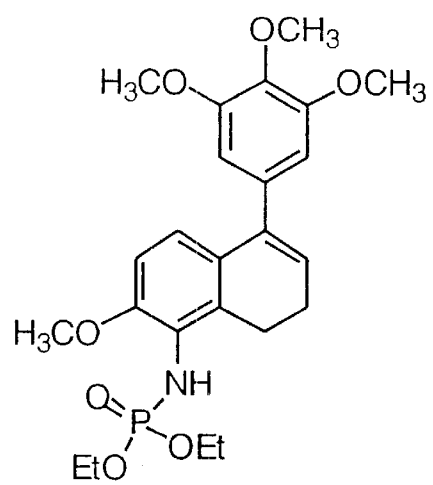
Figure 14:
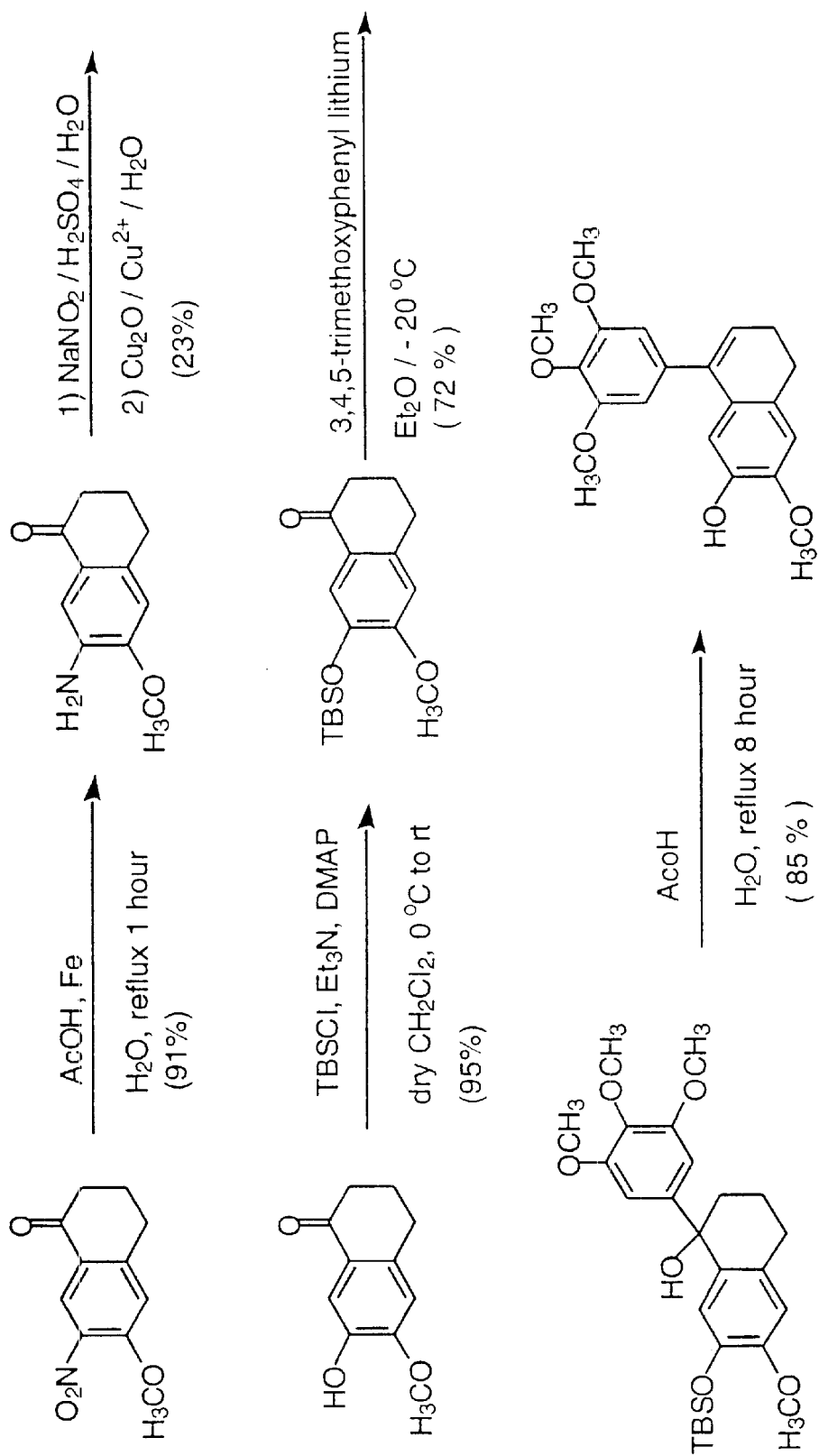
FIG. 14 shows preparation of 7-hydroxy-dihydronaphthalene ligand.

We have recently prepared a hydroxy-dihydronaphthalene analog based on the promising biological activity displayed by the related amino analog 15 (FIG. 3). The synthesis is detailed in FIG. 14. It should be obvious to anyone skilled in the art that phosphate salts and esters of this phenolic derivative (and related phenolic analogs) can readily be prepared using the various methodologies described herein. In addition, similar dihydronaphthalenes functionalized in an analogous fashion at the C-5 position can readily be prepared.

Figure 15:
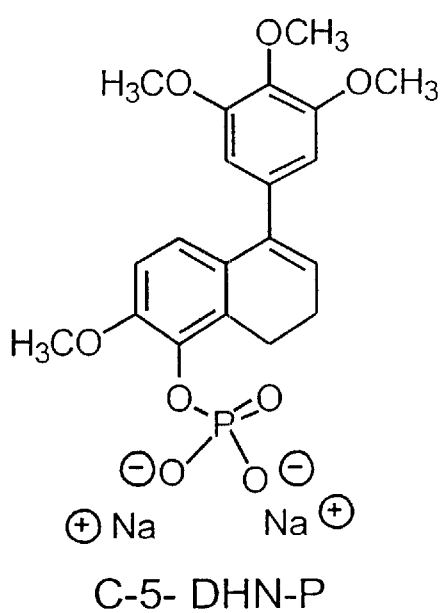
FIG. 15 shows dihydronapthalene-based prodrugs.
Figure 15:
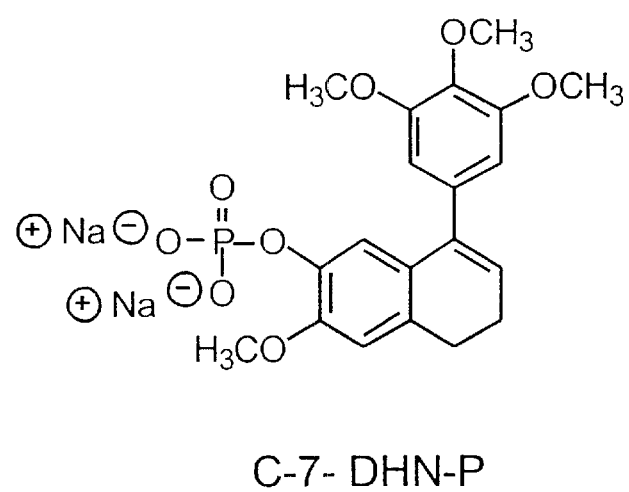
Figure 16:
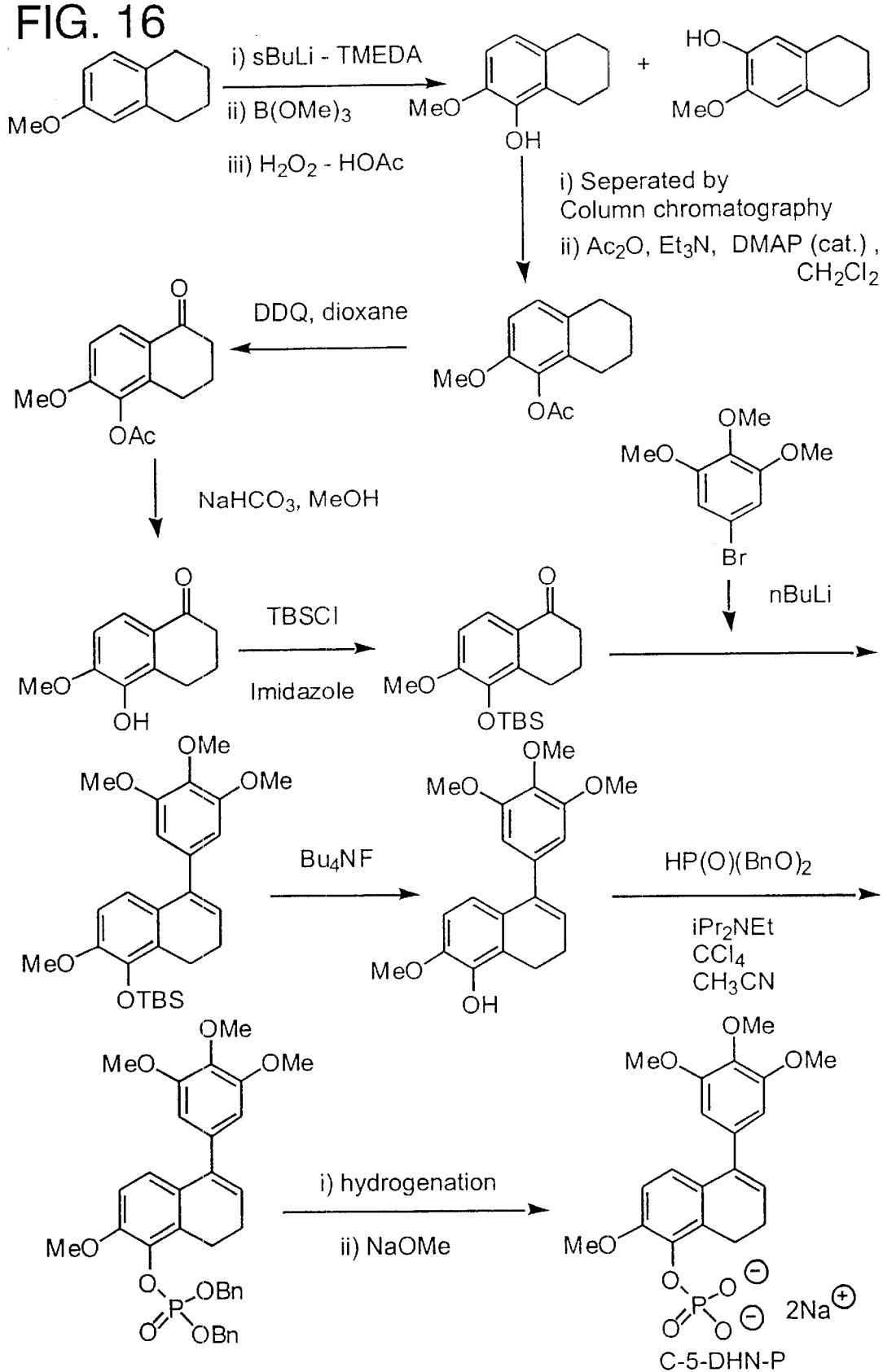
FIG. 16 shows preparation of C-5-DHN-P.

Furthermore, we have developed a synthetic route which will readily yield the C-5 and C-7 disodium phosphate salt and related phosphate derivatives of the 1-trimethoxyphenyl-dihydronapthalene system (FIGS. 15 and 16).

Figure 17:
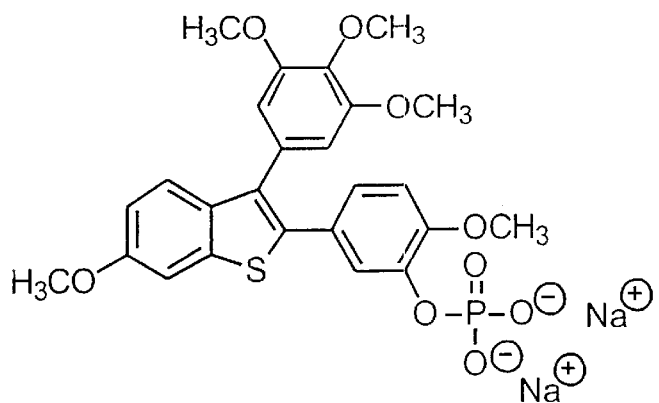
FIG. 17 shows diarylbenzo[b]thiophene prodrug constructs.
Figure 17:
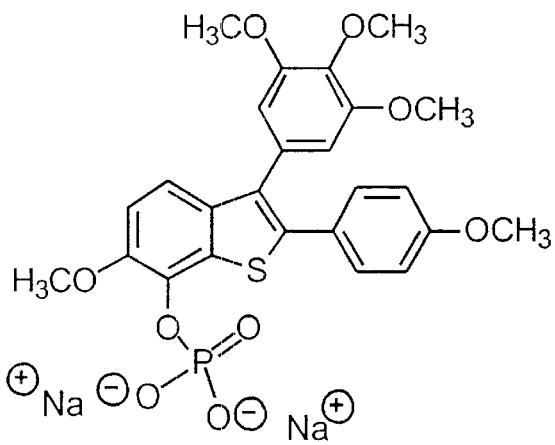
Figure 17:
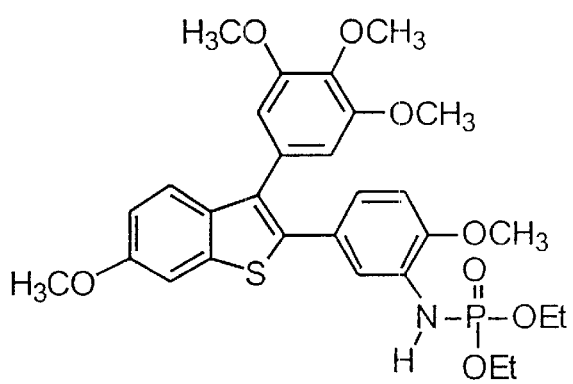
Figure 17:
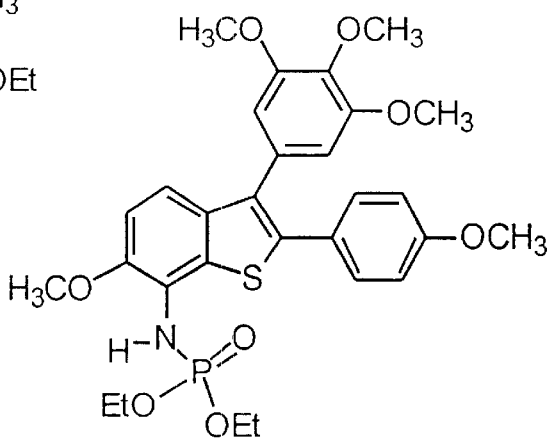
Figure 18:
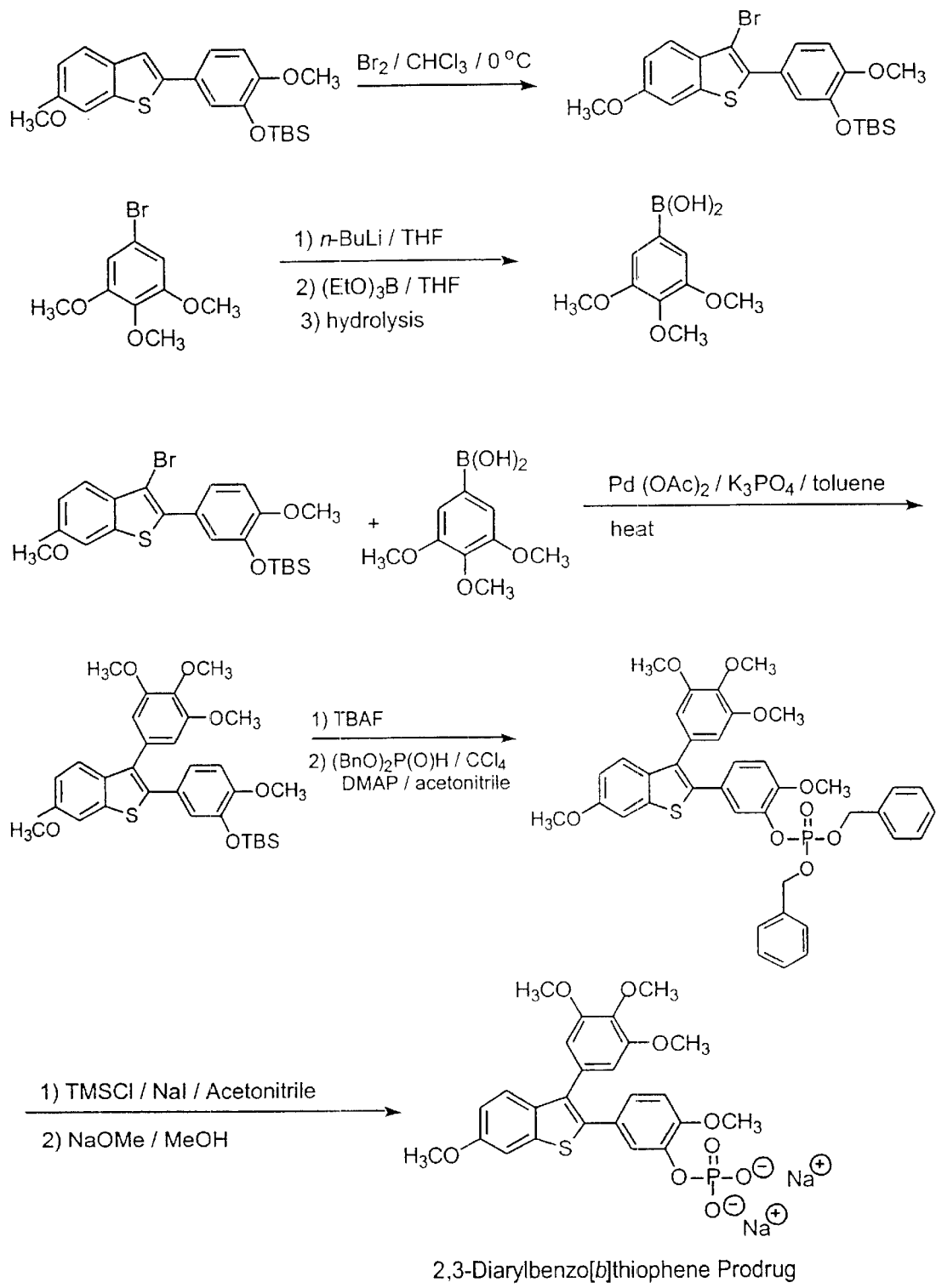
FIG. 18 shows preparation of 2,3-diarylbenzo[b]thiophene prodrug.

Based in part on the excellent biological activity of the dihydronaphthalene ligands, a logical extension of the work with the benzo[b]thiophene analogs involves the preparation of these ligands without the carbonyl group (see FIG. 17). A representative synthesis, which utilizes a Suzuki Coupling reaction as a key synthetic step, of this type of 2,3-diarylbenzo[b]thiophene prodrug is illustrated in FIG. 18. A very similar methodology can be employed by persons skilled in the art to prepare related compounds which vary in the position and number of phenolic moieties and phosphate salt moieties and/or amine groups and phosphoramidate groups around the core 2,3-diarylbenzo[b]thiophene ring system. It should be noted that the phenolic precursor to one of these compounds has recently been prepared by Flynn and co-workers in Australia but no mention has been made of the prodrug constructs[71]. In addition, Flynn has recently published (same reference as above) the phenolic precursor to one of the prodrugs illustrated in FIG. 1, however Flynn carefully (and accurately) mentions in this particular paper that Pinney and co-workers have also reported the same compound. The priority date of this patent clearly is well ahead of the publication of Flynn's work in this area. In addition, it should be noted once again that Flynn's work does not incorporate the prodrug motifs which seem especially important in the vascular targeting of tumor microvessels.

Diphosphate Prodrugs

Figure 19:
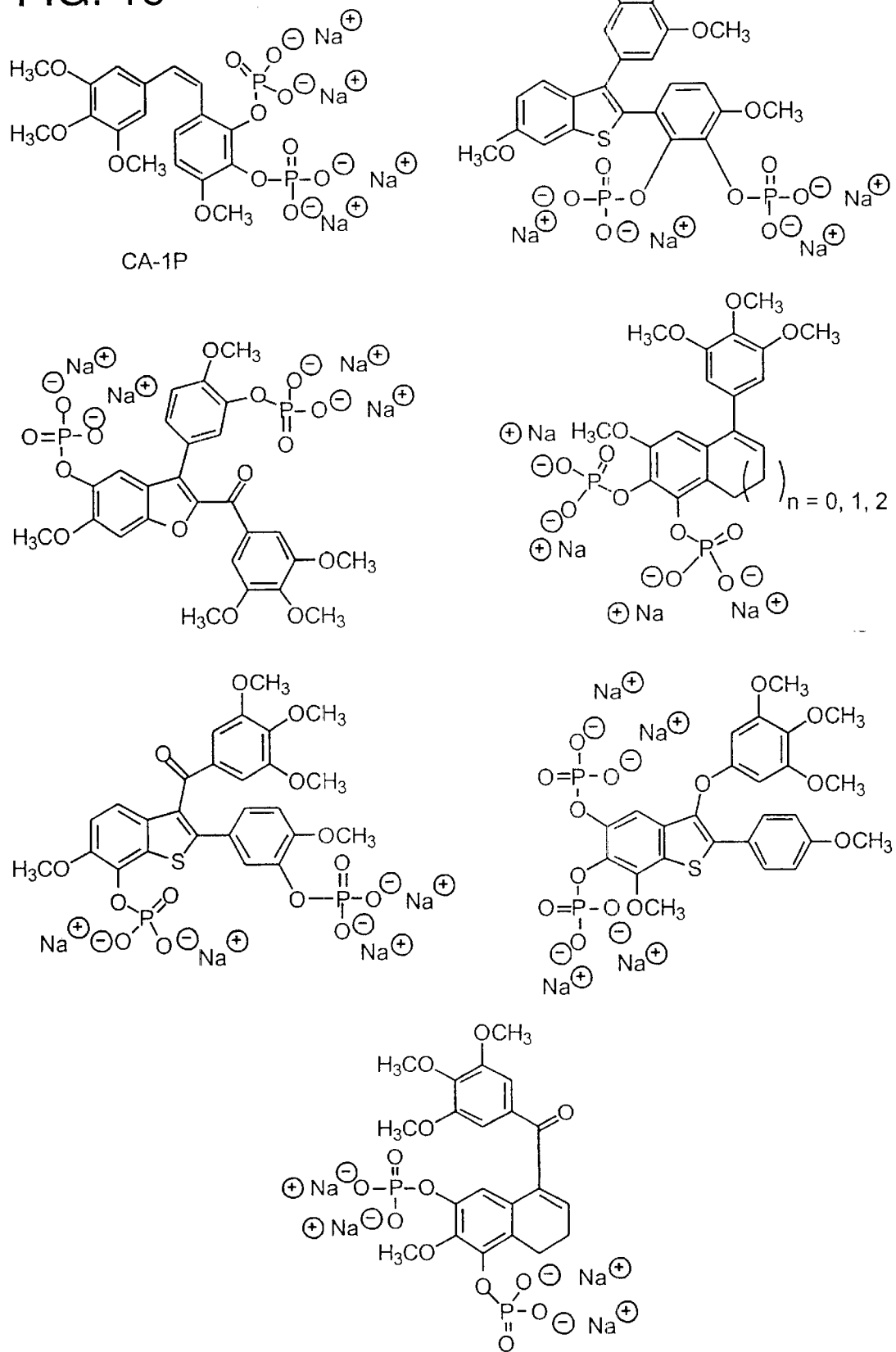
FIG. 19 is representative diphosphate vascular targeting agents.

It is now known that while CA-4P (FIG. 1B) is a potent vascular targeting and destruction agent in vivo it is likely that CA-1P (diphosphate)[72] may prove to be as active as CA-4P or even more active than CA-4P in vivo. Since CA-4P is enzymatically converted to CA-4 (in vivo) which in turn interacts with tubulin to cause the vascular disruption, it is reasonable to expect that the new tubulin binding ligands described in this application may prove to be enhanced vascular targeting and destruction agents once functionalized as diphosphates. A representative sampling of compounds of this nature is illustrated in FIG. 19. The syntheses of these compounds will parallel the methodology described in the various synthetic schemes delineated within this application and will be readily apparent to persons skilled in the art.

In Vivo Results with Benzo[b]thiophene Prodrug 3

Figure 20:
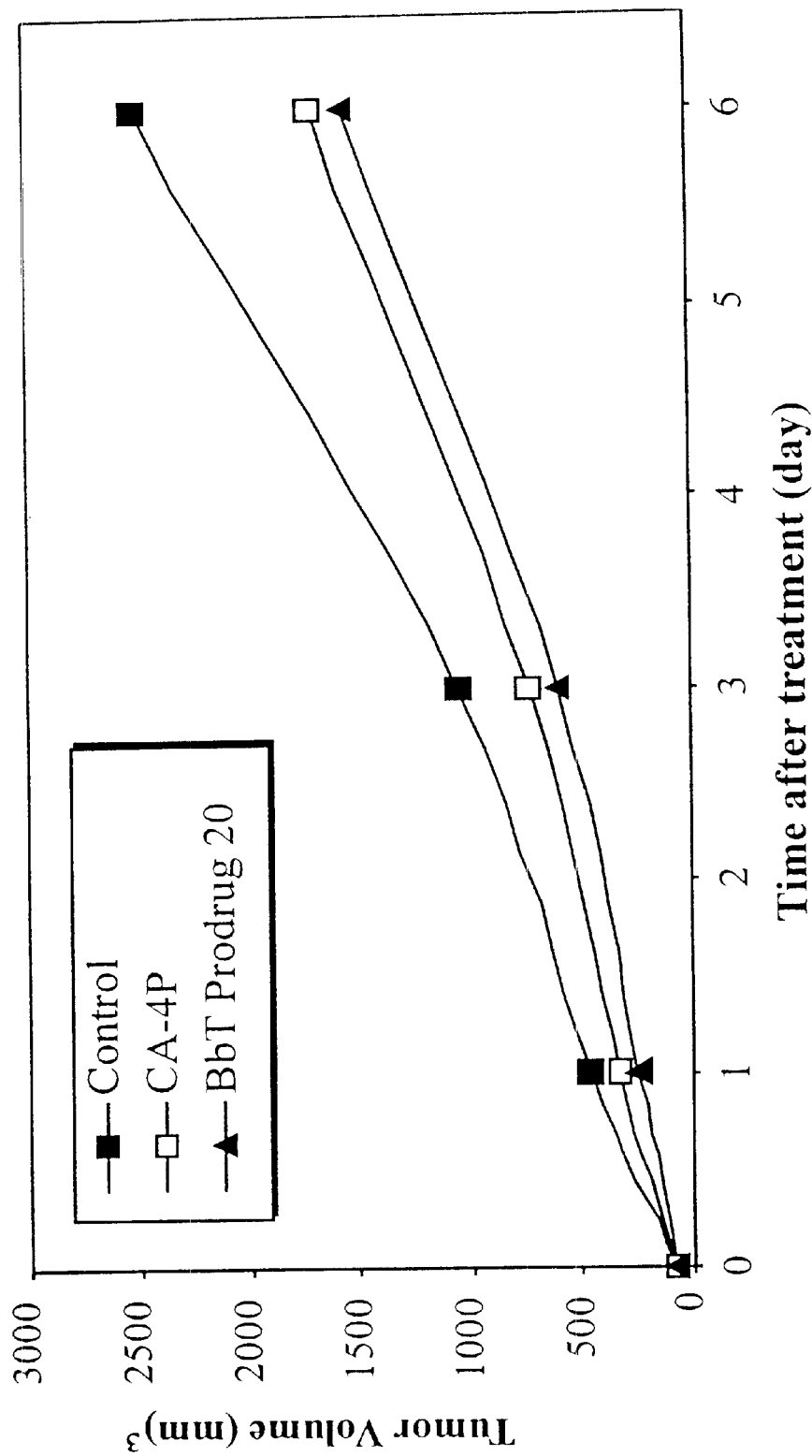
FIG. 20 is a graph showing in vivo biological data for benzo[b]thiophene prodrug 3.

Female scid mice were single dose ip administered with CA-4P, and benzo[b]thiophene phosphate prodrug at 400 mg/kg (i.e., MDT of CA-4P) after one week of MHEC inoculation (1×10⁶/mouse) (FIG. 20). Studies were carried out through a collaboration with professors Ronald W. Pero and Klaus Edvardsen, University of Lund, Sweden As described in FIG. 20, the benzo[b]thiophene prodrug 3 demonstrates remarkable activity in terms of tumor growth control in the skid mouse which is comparable to the activity demonstrated by combretastatin A-4P (CA-4P) which is currently in human clinical trials. It is important to note that this particular experiment shows only data for a single dose at 400 mg/kg. It is logical to expect that the other prodrug constructs described in this application may show similar or superior in vivo activity as compared to benzo[b]thiophene prodrug 3.

EXAMPLES

The following examples further illustrate embodiments of the present invention including preferred versions and methods of making the same; however these examples are not to be construed as limitations of this invention.

Example 1

Synthesis of the Benzo[b]thiophene Prodrug Construct 2-(3'-hydroxy-4'-methoxyphenyl)-6-methoxybenzo[b]thiophene (10).

Sulfide 9 (0.417 g, 0.996 mmol) and polyphosphoric acid (30 g) were combined in a 3 neck round bottom flask and stirred (mechanically) under nitrogen at 30–35° C. After 1 h, the reaction was quenched with ice water followed by work up with $CH_2Cl_2$. The organic layer was washed throughly with water and dried over $MgSO_4$. Removal of solvent, followed by purification by column chromatography (80:20 hexanes:EtOAc) yielded the cyclized product 10 with the deprotected hydroxy group (0.252 g, 0.880 mmol, 88%) as a yellow colored solid.

$^1$H-NMR ($CDCl_3$, 360 MHz) δ 7.80 (d, J=8.87 Hz, 1H, Ar$\underline{H}$), 7.36 (d, J=2.34 Hz, 1H, Ar$\underline{H}$), 7.17 (d, J=2.09 Hz, 1H, Ar$\underline{H}$), 7.16 (s, 1H, Ph—C$\underline{H}$=C), 7.07 (dd, J=8.24 Hz, 2.1 Hz, 1H, Ar$\underline{H}$), 7.01 (dd, J=8.89 Hz, 2.40 Hz, 1H, Ar$\underline{H}$), 6.95 (d, J=8.28 Hz, 1H, Ar$\underline{H}$), 5.70 (s, 1H, —O$\underline{H}$), 3.96, (s, 3H, —OC$\underline{H}_3$), 3.89 (s, 3H, —OC$\underline{H}_3$).

3-(3',4',5'-trimethoxybenzoyl)-2-(3'-tert-butyldimethylsilyloxy-4'-methoxyphenyl)-6methoxybenzo[b]thiophene.

To a well-stirred solution of 2-(3'-tert-butyldimethylsilyloxy-4'-methoxy phenyl)-6-methoxybenzo[b]thiophene 11 (0.105 g, 0.262 mmol), at 0° C., under nitrogen was added 3,4,5-trimethoxybenzoyl chloride (0.102 g, 0.442 mmol) followed by $AlCl_3$ (0.112 g, 0.839 mmol). The reaction mixture was brought to room temperature and stirred for 1.5 h. The reaction was then quenched with water followed by extraction with $CH_2Cl_2$, organic layer was washed with brine and dried over $MgSO_4$. Solvent removal followed by purification by column chromatography (gradual increase in polarity of the solvent from 90%, 80%, 50% Hexanes: EtOAc mixture) afforded the TBS-protected product (0.127 g, 0.226 mmol, 86%) as a yellow colored oil. A small amount of deprotected product was observed as well.

3-(3',4',5'-trimethoxybenzoyl)-2-(3'-hydroxy-4'-methoxyphenyl)-6-methoxybenzo[b]thiophene (2).

To a well-stirred solution of 3-(3',4',5'-trimethoxybenzoyl)-2-(3'-tert-butyldi-methylsilyloxy-4'-methoxyphenyl)-6-methoxybenzo[b]thiophene (0.127 g, 0.226 mmol) in $CH_2Cl_2$ (10 mL) at 0° C., under nitrogen was added TBAF (1M in THF, 0.350 mL, 0.350 mmol). The reaction mixture was brought to room temperature and stirred for 1 hr. The reaction mixture was then quenched with water followed by the usual work-up (EtOAc, brine, and drying over $MgSO_4$).

Removal of solvent followed by purification by column chromatography, afforded the desired hydroxy benzo[b]thiophene (0.049 g, 0.102 mmol, 45%) as a yellow colored solid.

$^1$H-NMR ($CDCl_3$, 360 MHz) δ 7.71 (d, J=9.01 Hz, 1H, Ar$\underline{H}$), 7.36 (d, J=2.29 Hz, 1H, Ar$\underline{H}$), 7.03 (dd, J=2.38 Hz, 9.01 Hz, 1H, Ar$\underline{H}$), 6.89 (d, J=1.99 Hz, 1H, Ar$\underline{H}$), 6.86 (s, 2H, Ar$\underline{H}$), 6.70 (dd, J=1.99 Hz, 8.21 Hz, 1H, Ar$\underline{H}$), 6.65 (d, J=8.22, 1H, Ar$\underline{H}$), 5.57 (s, 1H, O$\underline{H}$), 3.93 (s, 3H, —OC$\underline{H}_3$), 3.83 (s, 3H, —OC$\underline{H}_3$), 3.79 (s, 3H, —OC$\underline{H}_3$), 3.77 (s, 6H, —OC$\underline{H}_3$)

$^{13}$C-NMR ($CDCl_3$, 75 MHz) δ 190.4, 159.5, 152.4, 146.4, 145.2, 142.8, 141.3, 141.2, 135.2, 133.2, 127.8, 126.2, 122.5, 116.2, 115.8, 110.3, 106.9, 104.2, 60.7, 56.0, 55.9, 55.7. HRMS (EI) M⁺ calcd for $C_{26}H_{24}O_7S$ 480.1243, found 452.1230.

Anal. calcd for C$_{26}$H$_{24}$O$_7$S: C, 64.99; H, 5.03; S, 6.67. Found: C,64.85; H, 5.15; S, 6.58.

3-(3',4',5'-trimethoxybenzoyl)-2-(3'-benzylphosphate-4'-methoxyphenyl)-6-methoxybenzo[b]thiophene (12).

To a well-stirred solution of 3-(3',4',5'-trimethoxybenzoyl)-2-(3'-hydroxy-4'-methoxyphenyl)-6-methoxybenzo[b]thiophene (0.037 g, 0.077 mmol), under N$_2$ in acetonitrile (1 mL) at −25° C. was added CCl$_4$ (1 mL). After stirring for 10 min, ethyldiisopropylamine (0.030 mL, 0.164 mmol) and DMAP (0.010 g) were added. Dibenzylphosphite (0.030 mL, 0.136 mmol) was added after 5 min and the mixture was stirred at −20° C. for 1.5 h. The reaction mixture was slowly warmed to room temperature and stirred for an additional 2 h at which time KH$_2$PO$_4$ was added and the product was isolated by extraction with EtOAc. The organic layer was washed with water and brine, and dried over MgSO$_4$. Following solvent evaporation, purification by column chromatography (gradual increase of solvent polarity from 70% to 60% hexanes:EtOAc) yielded the desired phosphate (0.031 g, 0.042 mmol, 55%) as a yellowish-white thick liquid.

$^1$H-NMR (CDCl$_3$, 360 MHz) δ 7.63 (dd, J=9.01 Hz, 0.34 Hz, 1H, ArH), 7.35 (d, J=2.24 Hz, 1H, ArH), 7.29 (m, 10H, ArH), 7.19 (dd, J=2.06 Hz, 1H, 2.05 Hz, ArH), 7.04 (ddd, J=8.41 Hz, 2.11 Hz, 2.10 Hz, 1H, ArH), 7.00 (dd, 9.01 Hz, 2.38 Hz, 1H, ArH), 6.87 (s, 2H, ArH), 6.78 (dd, J=8.51 Hz, 0.85 Hz, 1H, ArH), 5.14 (d, J=8.06 Hz, 4H, —CH$_2$), 3.93 (s, 3H, —OCH$_3$), 3.79 (s, 3H, —OCH$_3$), 3.75 (s, 3H, —OCH$_3$), 3.73 (s, 6H, —OCH$_3$).

$^{31}$P-NMR (CDCl$_3$, 145 MHz) δ (−5.34).

LRMS (EI) M$^+$ found for C$_{40}$H$_{37}$O$_{10}$SP: 740.534.

3-(3',4',5'-trimethoxybenzoyl)-2-(3'-sodiumphosphate-4'-methoxyphenyl)-6-methoxybenzo[b]thiophene (3).

To a well-stirred solution of dibenzyl ester 12 (0.100 g, 0.141 mmol) in dry acetonitrile (6 mL) was added sodium iodide (0.0423 g, 0.282 mmol). Chlorotrimethylsilane (0.03 g, 0.024 mL, 0.282 mmol) was slowly added to this solution. After 30 min, water was slowly added until all of the visible salts were dissolved. The straw color was removed upon the addition of a sodium thiosulphate (10%) solution. The organic phase was separated, and the aqueous phase was extracted with ethyl acetate (4×50 mL). The combined organic layer was concentrated in vacuo to give a pale yellow foam which was dissolved in dry methanol (5 mL). To this solution was added sodium methoxide (0.0152 g, 0.282 mmol) in one portion. After stirring for 9 h, the methanol was removed in vacuo and the resultant solid was recrystallized from H$_2$O/acetone to afford the disodium salt (0.040 g, 0.066 mmol, 47%) as a pale yellow powder.

$^1$H-NMR (DMSO, 300 MHz) δ 3.62 (s, 3H), 3.66 (s, 3H), 3.70 (s, 6H), 3.89 (s, 3H), 6.67 (m, 2H), 6.80 (s, 2H), 7.15 (d, J=11.1 Hz, 1H), 7.69 (m, 2H), 7.84 (d, J=1.1, 1H).

$^{13}$C-NMR (DMSO, 75 MHz) δ 56.3, 56.5, 56.7, 60.8, 105.7, 107.4, 112.6, 116.7, 122.4, 124.4, 126.6, 127.3, 133.5, 133.7, 134.9, 141.5, 142.5, 142.8, 144.4, 144.5, 150.5, 150.6, 152.9, 160.0, 190.7.

$^{31}$P-NMR (DMSO, 300 MHz) δ −1.94

Example 2
Large-scale Preparations 3-tert-butyldimethylsiloxy-4-methoxybenzaldehyde.

To a 1-L round-bottom flask was added isovanillin (80 g, 526 mmol), DMAP (1 g) and a large magnetic stir bar, and the flask was put under inert atmosphere. Dry dichloromethane (~450 mL) was added, followed by triethylamine (81 mL, 580 mmol), at which point the solid entirely dissolved. The mixture was cooled to 0° C. and tert-butyldimethylsilyl chloride (89 g, 590 mmol) was added in one portion. The mixture began almost immediately to precipitate solid. The mixture was allowed to stir for 1.5 h at 0° C., at which point TLC (30% EtOAc/hexanes) showed an almost complete absence of isovanillan. The mixture was allowed to stir overnight, then the precipitate was filtered off through Celite. The filtrate was washed with water (200 mL) followed by saturated NaCl solution (200 mL) and dried over MgSO4. This was filtered into a tared 1-L flask and concentrated by distillation on a rotary evaporator, followed by aspirator vacuum to approximately constant weight, yielding a deep red-brown liquid (149.4 g; theoretical=140 g). This material was taken into the next reaction without further characterization.

1-(3-tert-butyldimethylsiloxy-4-methoxyphenyl)ethanol.

The entire crude product from the preceding reaction (~526 mmol) was transferred as a solution in dry ether (200 mL) to a 2-L round bottom flask equipped with a very large magnetic stirring bar. An additional 500 mL of dry ether were added and the mixture was cooled to 0° C. Then methyllithium (500 mL of a 1.4 M solution, 700 mmol) was added over ~40 minutes by cannula, and the mixture was allowed to stir overnight. The deep red mixture was re-cooled to 0° C. and treated with water (200 mL) very cautiously at first. The mixture became a heterogeneous yellow. In a separatory funnel, the aqueous phase was separated and the organic phase was washed once with saturated NaCl solution and dried over MgSO4. After filtration and concentration by distillation on a rotary evaporator followed by aspirator vacuum, a deep red liquid was obtained (136.8 g), and was found to be free of starting material by TLC. This material was taken into the next reaction without further characterization.

3-tert-butyldimethylsiloxy-4-methoxyacetophenone.

The entire amount of the crude alcohol from the preceding reaction was transferred to a 3-L round bottom flask as a solution in ~1.5 L of dry dichloromethane. Celite (62 g, oven dried), K$_2$CO$_3$ (16 g) and a very large magnetic stirring bar were added. Then PCC (115 g) was added in portions over a 2-hr period, during which time the heterogeneous yellow mixture became dark brown. At the end of the addition, large amounts of the starting alcohol were still present by TLC (25% EtOAc/hexanes) so the mixture was allowed to stir overnight. At this point, the starting alcohol was absent (or nearly so) by TLC, and the mixture was filtered through a 3-cm pad of silica gel, rinsing well with dichloromethane. The mud-brown solution was concentrated by distillation on a rotary evaporator followed by aspirator vacuum to yield a opaque brown liquid. This was purified in 30 mL portions by Kugelrohr distillation (~0.5 Torr, 140° C.) to yield 104.4 g of a brown liquid which crystallized on brief standing. This was dissolved in hot hexanes (104 mL) and filtered hot through Celite to yield a clear yellow solution. This was seeded and left in a refrigerator (~5° C.) overnight. The crystalline product was filtered cold, washed quickly with a small amount of cold hexanes and dried under pump vacuum to give 84.8 g (303 mmol, 58% yield from isovanillin) of light yellow solid, pure by $^1$H and $^{13}$C NMR. A second crop of crystals (6.3 g) were obtained by dissolving the concentrated filtrate in hot hexanes (20 mL) followed by seeding and standing overnight.

$^1$H NMR (CDCl$_3$): 0.15 (s, 6H); 0.98 (s, 9H); 2.52 (s, 3H); 3.85 (s, 3H); 6.85 (d, 1H, J=8.4); 7.45 (s, 1H); 7.56 (dd, 1H, J=8.4, 2.2).

$^{13}$C NMR (CDCl$_3$): −4.8, 18.4, 25.6, 26.3, 55.4, 110.7, 120.2, 123.5, 130.5, 144.7, 155.3, 196.8.

This important important part of the present invention is a new efficient method of converting 3-(tert-butyldimethylsiloxy)-4-methoxyacetophenome to α-halo-3-(tert-butyldimethylsiloxy)-4-methoxyacetophenome by treatment of the trimethylsilyl enol ether [1-(3-(tert-butyldimethylsiloxy)-4-methoxyphenyl)-1-trimethylsiloxyethylene] with elemental halogen. Bromine is preferred as the halogen which converts the final compound to α-bromo-3-(tert-butyldimethylsiloxy)-4-methoxyacetophenone. It is understood that chlorine and iodine may be utilized in place of bromine should iodo or chloro analogs be desired.

Example 3

Synthesis of Dihydronaphthalene Phosphoramidate Prodrug

6-Methoxy-5-Nitro-1-Tetralone and 6-Methoxy-7-Nitro-1-Tetralone

To an ice-cold, stirred sloution of 6-methoxy-1-tetralone (17.6 g, 0.10 mol) in acetone (30 mL) was added dropwise a mixture of sulfuric acid (18 mL, 96.0%) and nitric acid (15 mL, 68.0-70.0%). After the addition was complete, the reaction was stirred at 0° C. for 6 hours, and TLC was employed to monitor the reaction progress. The reaction mixture was poured into ice-water, and the mixture was partitioned between $CH_2Cl_2$ (3*200 mL) and water (200 mL). The organic layer was washed by saturated $NaHCO_3$ solution and water (200 mL each), dried over anhydrous sodium sulfate, and, after filtration, the organic layer was concentrated in vacuo to provide a yellow oil. 6-Methoxy-5-nitro-1-tetralone (7.74 g, 0.035 mol) and 6-methoxy-7-nitro-1-tetralone (6.63 g, 0.030 mol) was obtained after purification by column chromatography.

6-Methoxy-5-nitro-1-tetralone:

$^1$H-NMR ($CDCl_3$, 300 MHz) δ 2.15 (m, 2H), 2.65 (t, J=6.2 Hz, 2H), 2.87 (t, J=6.0 Hz, 2H), 7.02 (d, J=8.7 Hz, 1H), 8.19 (d, J=8.9 Hz, 1H).

6-Methoxy-7-nitro-1-tetralone:

$^1$H-NMR ($CDCl_3$, 300 MHz) δ 2.15 (m, 2H), 2.67 (t, J=6.2 Hz, 2H), 3.01 (t, J=6.1 Hz, 2H), 6.90 (s, 1H), 8.52 (s, 1H).

5-Amino-6-methoxy-1-(3',4',5'-trimethoxyphenyl)-3,4-dihydronaphthalene 15

To a stirred solution of n-butyllithium (15.0 mL, 1.6 M in hexane solution, 24.0 mmol) in dry ether (160 mL), a solution of 3,4,5-trimethoxyphenylbromide (2.97 g, 12.0 mmol) in ether (40 mL) was added under dry nitrogen at −78° C. The solution was stirred for 1 h in order to form 3,4,5-trimethoxyphenyllithum. 6-Methoxy-5-nitro-1-tetralone (2.65 g, 12.0 mmol) was added at −20° C., and the stirring was continued for 2 h (−20° C.-rt). The mixture was partitioned between $CH_2Cl_2$ and water, the organic layer was dried over anhydrous sodium sulfate, and, after filtration, the organic layer was concentrated in vacuo, to afford 1-Hydroxy-6-methoxy-5-nitro-1-(3',4',5'-trimethoxyphenyl) tetralin 17 as a crude yellow oil. (GC-MS shows the yield is about 55%) This compound, without purification, was added to a refluxing mixture of acetic acid (10 mL) and water (80 mL), and iron (0.5 g) was added. After heating at reflux for 1 h, the mixture was partitioned between $CH_2Cl_2$ (3*100 mL) and water (100 mL). The organic layer was washed with $NaHCO_3$ (sat.) and water (100 mL each), dried over anhydrous sodium sulfate, and, after filtration, the organic layer was concentrated in vacuo to provide a yellow oil. Purification by column chromatography afforded 5-Amino-6-methoxy-1-(3',4',5'-trimethoxyphenyl)-3,4-dihydronaphthalene 15 (2.03 g, 5.95 mmol). $^1$H-NMR ($CDCl_3$, 300 MHz) δ 2.43 (m, 2H), 2.68 (t, J=7.8 Hz, 2H), 3.84 (s, 6H), 3.86 (s, 3H), 3.89 (s, 3H), 5.93 (t, J=4.7 Hz, 1H), 6.51 (d, J=8.4 Hz, 1H), 6.56 (s, 2H), 6.60 (d, J=8.4 Hz, 1H). $^{13}$C-NMR ($CDCl_3$, 75 MHz) δ 22.0, 23.3,56.0, 56.5, 61.3, 106.4, 107.5, 117.2, 121.6, 124.5, 128.6, 132.8, 137.4, 137.6, 140.4, 147.5, 153.2. HRMS (EI) M$^+$, calcd for $C_{20}H_{23}NO_4$ 341.1627, found 341.1635. Anal. Calcd for $C_{20}H_{23}NO_4$: C, 70.36; H, 6.79; N: 4.10. Found: C, 70.24; H, 6.74; N, 4.08.

6-methoxy-1-(3',4',5'-trimethoxyphenyl)-5-diethylphosphoramidate-3,4-dihydronaphthalene 16

To a stirred solution of $ClP(OC_2H_5)_2$ (0.157 g, 1.0 mmol) in dry ethyl ether (20 mL) was added slowly a solution of 5-Amino-6-methoxy-1-(3',4',5'-trimethoxyphenyl)-3,4-dihydronaphthalene (0.341 g, 1 mmol) in dry ethyl ether (30 mL) at −78° C. Once this addition was complete, a solution of N,N-diisopropylethylamine (0.28 g, 2.2 mmol) in dry ethyl ether (2 mL) was added. The solution was stirred at −78° C. for 2 hours, followed by stirring at rt for 10 hours. The solution was fitered and concentrated in vacuo to provide a yellow oil. The yellow oil was dissolved in dry $CH_2Cl_2$ (10 mL), then cooled to −40° C. A solution of MCPBA (0.28 g) in dry $CH_2Cl_2$ (10 mL) was added. After stirring at rt for 1 h, the organic layer was washed with saturated $Na_2SO_4$ solution and water (10 mL each), dried over anhydrous sodium sulfate, and, after filtration, the organic layer was concentrated in vacuo to provide a yellow oil. Purification by column chromatography afforded 6-methoxy-1-(3',4',5'-trimethoxyphenyl)-5-diethylphosphoramidate-3,4-dihydronaphthalene 16 (0.286 g, 0.60 mmol). $^1$H-NMR ($CDCl_3$, 300 MHz) δ 1.33 (t, J=7.0 Hz, 6H), 2.75 (t, J=8.5 Hz, 2H), 3.21 (t, J=8.6 Hz, 2H), 3.82 (s, 3H), 3.84 (s, 6H), 3.92 (s, 3H), 4.11 (m, 4H), 6.46 (s, 2H), 6.50 (d, J=8.4 Hz, 1H), 6.57 (d, J=8.6 Hz, 1H). $^{13}$C-NMR ($CDCl_3$, 75 MHz) δ 16.2, 16.3, 24.8, 32.4, 55.6, 56.2, 61.0, 62.9, 63.0, 107.0, 107.6, 123.7, 124.7, 129.1, 131.4, 133.4, 134.8, 152.8, 153.1. $^{31}$P-NMR($CDCl_3$, 300 MHz) δ 6.51. HRMS (EI) M$^+$, calcd for $C_{24}H_{32}NPO_7$477.1916, found 477.1928.

Example 4

Synthesis of Dihydronaphthalene and Indene Analogs

Synthesis of Compounds 18, 14A, 19, 22, 23, 24, 25 (General Procedure):

To a stirred solution of n-butyllithium (3.7 mL, 1.6 M in hexane solution, 6.0 mmol) in dry ether (40 mL), a solution of 3,4,5-trimethoxyphenylbromide (0.74 g, 3.0 mmol) in ether (20 mL) was added under dry nitrogen at −78° C. The solution was stirred for 1 h in order to form 3,4,5-trimethoxyphenyllithum. The ketone reagent (3.0 mmol) was added at −20° C., and the stirring was continued for 2 h (−20° C.-rt). The mixture was partitioned between $CH_2Cl_2$ and water, the organic layer was dried over anhydrous sodium sulfate, and, after filtration, the organic layer was concentrated in vacuo to provide a yellow oil. The compound was purified by column chromatography.

Synthesis of Compounds 20, 14B, 21, 26, 27, 28, 29 (General Procedure):

To a solution of acetic acid (10 mL) in $H_2O$ (60 mL), compound 18, 14A, 19, 22, 23, 24, 25 (1 mmol) was added respectively. The solution was heated to reflux for 1 hour, and then cooled down to rt. $NaHCO_3$ (20 mL, saturated solution) was added, and the mixture was partitioned between $CH_2Cl_2$ and water. The organic layer was dried over anhydrous sodium sulfate, after filtration, the organic layer was concentrated in vacuo to provide a yellow oil. The compound was purified by column chromatography.

Yield of the compounds: 18, 61%; 14A, 58%; 19, 41%; 20, 92%; 14B, 90%; 21, 90%; 22, 56%; 23, 54%; 24, 50%; 25, 45%; 26, 91%; 27, 90%; 28, 90% 29, 84%.

Data for compounds

18. $^1$H-NMR (CDCl$_3$, 300 MHz) δ 1.82 (m, 1H), 1.96 (m, 1H), 2.10 (t, J=5.7 Hz, 2H), 2.82 (t, J=5.9 Hz, 2H), 3.68 (s, 3H), 3.78 (s, 6H), 3.85 (s, 3H), 6.55 (s, 2H), 6.22 (d, J=2.6 Hz, 1H), 6.80 (dd, J=2.7, 8.4 Hz, 1H), 7.08 (d, J=8.4 Hz, 1H). $^{13}$C-NMR (CDCl$_3$, 75 MHz) δ 14.1, 19.8, 28.9, 41.3, 55.3, 56.1, 60.8, 75.7, 103.8, 113.0, 114.3, 129.7, 129.9, 136.5, 142.6, 144.4, 152.5, 157.9. HRMS (EI) M$^+$, calcd for C$_{20}$H$_{24}$O$_5$ 344.1624, found 344.1622.

14A. $^1$H-NMR (CDCl$_3$, 300 MHz) δ 1.82 (m, 1H), 2.00 (m, 4H), 2.88 (t, J=6.2, 2H), 3.79 (s, 6H), 3.80 (s, 3H), 3.85 (s, 3H), 6.57 (s, 2H), 6.69 (m, 2H), 6.99 (d, J=7.5 Hz, 1H). $^{13}$C-NMR (CDCl$_3$, 75 MHz) δ 19.7, 30.2, 41.4, 55.2, 56.1, 60.8, 75.2, 103.7, 112.8, 112.9, 130.2, 134.1, 136.4, 139.1, 144.9, 152.5, 158.7. HRMS (EI) M$^+$, calcd for C$_{20}$H$_{24}$O$_5$ 344.1624, found 344.1626.

19. $^1$H-NMR (CDCl$_3$, 300 MHz) δ 1.84 (m, 1H), 2.00 (m, 1H), 2.12 (m, 2H), 2.22 (s, 1H), 2.67 (m, 1H), 2.94 (m, 1H), 3.78 (s, 6H), 3.85 (s, 3H), 3.87 (s, 3H), 6.55 (s, 2H), 6.70 (d, J=8.0 Hz, 1H), 6.77 (d, J=8.1 Hz, 1H), 7.13 (t, J=7.9 Hz, 1H). $^{13}$C-NMR (CDCl$_3$, 75 MHz) δ 19.2,23.6,41.0, 55.7, 56.4, 61.1, 75.8, 104.1, 108.8, 120.9, 126.9, 127.1, 136.7, 143.0, 145.0, 152.8, 157.0. HRMS (EI) M$^+$, calcd for C$_{20}$H$_{24}$O$_5$ 344.1624, found 344.1622.

20. $^1$H-NMR (CDCl$_3$, 300 MHz) δ 2.83 (m, 2H), 2.79 (t, J=7.7 Hz, 2H), 3.71 (s, 3H), 3.85 (s, 6H), 3.89 (s, 3H), 6.11 (t, J=4.6 Hz, 1H), 6.57 (s, 2H), 6.65 (d, J=2.6 Hz, 1H), 6.73 (dd, J=2.6, 8.2 Hz, 1H), 7.13 (d, J=8.2 Hz, 1H). $^{13}$C-NMR (CDCl$_3$, 75 MHz) δ 24.1, 27.6, 55.7, 56.4, 61.3, 106.0, 112.0, 112.3, 128.4, 128.5, 129.2, 136.3, 136.7, 137.3, 140.1, 153.3, 158.4. HRMS (EI) M$^+$, calcd for C$_{20}$H$_{22}$O$_4$ 326.1518, found 326.1507. Anal. Calcd for C$_{20}$H$_{22}$O$_4$: C, 73.60; H, 6.79. Found: C, 73.77; H, 6.93.

14B. $^1$H-NMR (CDCl$_3$, 300 MHz) δ 2.83 (m, 2H), 2.83 (t, J=7.6 Hz, 2H), 3.82 (s, 3H), 3.85 (s, 6H), 3.89 (s, 3H), 5.95 (t, J=4.5 Hz, 1H), 6.56 (s, 2H), 6.66 (dd, J=2.6,8.4 Hz, 1H), 6.73 (d, J=2.6 Hz, 1H), 7.00 (d, J=8.4 Hz, 1H). $^{13}$C-NMR (CDCl$_3$, 75 MHz) δ 23.8, 29.2, 55.7, 56.5, 61.4, 106.1, 111.2, 114.2, 125.2, 127.1, 128.5, 137.1, 137.4, 139.0, 139.9, 153.4, 159.0. HRMS (EI) M$^+$, calcd for C$_{20}$H$_{22}$O$_4$ 326.1518, found 326.1515.

21. $^1$H-NMR (CDCl$_3$, 300 MHz) δ 2.39 (m, 2H), 2.86 (t, J=8.3 Hz, 2H), 3.84 (s, 6H), 3.87 (s, 3H), 3.89 (s, 3H), 6.10 (t, J=4.6 Hz, 1H), 6.55 (s, 2H), 6.71 (d, J=7.7 Hz, 1H), 6.82 (d, J=8.2 Hz, 1H), 7.11 (t, J=8.1 Hz, 1H). $^{13}$C-NMR (CDCl$_3$, 75 MHz) δ 19.8, 22.8, 55.6, 56.1, 60.9, 105.7, 109.7, 118.5, 124.5, 126.2, 127.7, 136.0, 136.8, 136.9, 139.7, 152.8, 156.0. HRMS (EI) M$^+$, calcd for C$_{20}$H$_{22}$O$_4$ 326.1518, found 326.1518. Anal. Calcd for C$_{20}$H$_{22}$O$_4$: C, 73.60; H, 6.79. Found: C, 73.77; H, 6.84.

22. $^1$H-NMR (CDCl$_3$, 300 MHz) δ 2.19 (s, 1H), 2.48 (m, 2H), 2.91 (m, 1H), 3.10 (m, 1H), 3.76 (s, 3H), 3.82 (s, 6H), 3.86 (s, 3H), 6.64 (s, 2H), 6.67 (d, J=2.4 Hz, 1H), 6.91 (dd, J=2.4, 6.5 Hz, 1H), 7.27 (d, J=6.5 Hz, 1H). $^{13}$C-NMR (CDCl$_3$, 75 MHz) δ 29.0, 45.4, 55.5, 56.1, 60.8, 85.7, 102.9, 108.4, 115.2, 125.7, 135.9, 136.6, 141.9, 148.9, 152.8, 159.2. HRMS (EI) M$^+$, calcd for C$_{19}$H$_{22}$O$_5$ 330.1467, found 330.1466.

23. $^1$H-NMR (CDCl$_3$, 300 MHz) δ 2.12 (s, 1H), 2.48 (t, J=6.2 Hz, 2H), 2.90 (m, 1H), 3.15 (m, 1H), 3.81 (s, 6H), 3.84 (s, 3H), 3.86 (s, 3H), 6.65 (s, 2H), 6.78 (dd, J=2.3, 8.4 Hz, 1H), 6.86 (d, J=2.3 Hz, 1H), 7.04 (d, J=8.4 Hz, 1H). $^{13}$C-NMR (CDCl$_3$, 75 MHz) δ 30.0, 45.7, 56.0, 56.4, 61.2, 85.6, 103.4, 110.2, 113.7, 125.2, 137.0, 140.4, 142.8, 145.5, 153.2, 160.7. HRMS (EI) M$^+$, calcd for C$_{19}$H$_{22}$O$_5$ 330.1467, found 330.1470.

24. $^1$H-NMR (CDCl$_3$, 300 MHz) δ 2.18 (s, 1H), 2.50 (m, 2H), 2.95 (m, 1H), 3.07 (m, 1H), 3.80 (s, 6H), 3.85 (s, 3H), 3.89 (s, 3H), 6.64 (s, 2H), 6.75 (d, J=7.6 Hz, 1H), 6.82 (d, J=7.4 Hz, 1H), 7.22 (d, J=8.0 Hz, 1H). $^{13}$C-NMR (CDCl$_3$, 75 MHz) δ 26.6, 44.5, 55.3, 56.1, 60.8, 86.1, 103.0, 109.8, 116.0, 128.7, 131.9, 136.6, 142.1, 149.4, 152.8, 156.0. HRMS (EI) M$^+$, calcd for C$_{19}$H$_{22}$O$_5$ 330.1467, found 330.1466.

25. $^1$H-NMR (CDCl$_3$, 300 MHz) δ 2.11 (s, 1H), 2.49 (m, 2H), 2.90 (m, 1H), 3.09 (m, 1H), 3.79 (s, 3H), 3.80 (s, 6H), 3.86 (s, 3H), 3.92 (S, 3H), 6.62 (s, 2H), 6.65 (s, 1H), 6.85 (s, 1H). $^{13}$C-NMR (CDCl$_3$, 75 MHz) 630.1, 45.9, 56.4, 56.5, 61.2, 86.5, 103.3,106.8, 107.8, 136.5, 137.0, 139.5, 142.8, 149.0, 150.2, 153.2. HRMS (EI) M$^+$, calcd for C$_{20}$H$_{24}$O$_6$ 360.1573, found 360.1564.

26. $^1$H-NMR (CDCl$_3$, 300 MHz) δ 3.45 (d, J=1.3 Hz, 2H), 3.83 (s, 3H), 3.91 (s, 9H), 6.58 (t, J=1.9 Hz, 1H), 6.80 (s, 2H), 6.83 (dd, J=2.3, 8.2 Hz, 1H), 7.14 (d, J=2.3 Hz, 1H), 7.42 (d, J=8.2 Hz, 1H). $^{13}$C-NMR (CDCl$_3$, 75 MHz) δ 37.4, 55.5, 56.1, 60.9, 104.6, 106.1, 110.8, 124.5, 131.7, 132.1, 136.7, 137.5, 145.0, 145.2, 153.3, 158.8. HRMS (EI) M$^+$, calcd for C$_{19}$H$_{20}$O$_4$ 312.1362, found 312.1361. Anal. Calcd for C$_{19}$H$_{20}$O$_4$: C, 73.06; H, 6.45. Found: C, 73.21; H, 6.44.

27. $^1$H-NMR (CDCl$_3$, 300 MHz) δ 3.48 (s, 2H), 3.86 (s, 3H), 3.91 (s, 9H), 6.42 (s, 1H), 6.89 (s, 2H), 6.91 (dd, J=2.7, 7.8 Hz, 1H), 7.13 (d, J=2.7 Hz, 1H), 7.49 (d, J=8.0 Hz, 1H). $^{13}$C-NMR (CDCl$_3$, 75 MHz) δ 38.0, 55.6, 56.1, 60.9, 104.6, 110.6, 111.8, 12.5, 128.4, 132.0, 136.9, 137.5, 144.7, 146.6, 153.3, 158.0. HRMS (EI) M$^+$, calcd for Cl$_9$H$_{20}$O$_4$ 312.1362, found 312.1357. Anal. Calcd for Cl$_9$H$_{20}$O$_4$: C, 73.06; H, 6.45. Found: C, 72.98; H, 6.52.

28. $^1$H-NMR (CDCl$_3$, 300 MHz) δ 3.47 (d, J=1.9 Hz, 2H), 3.91 (s, 9H), 3.94 (s, 3H), 6.57 (t, J=1.9 Hz, 1H), 6.81 (s, 2H), 6.83 (d, J=8.2 Hz, 1H), 7.24 (d, J=7.6 Hz, 1H), 7.33 (d, J=7.7 Hz, 1H). $^{13}$C-NMR (CDCl$_3$, 75 MHz) δ 35.0, 54.9, 55.7, 60.5, 104.3, 107.0, 113.0, 127.5, 130.4, 131.2, 131.4, 137.0, 144.6, 145.2, 152.8, 155.1. HRMS (EI) M$^+$, calcd for Cl$_9$H$_{20}$O$_4$ 312.1362, found 312.1361. Anal. Calcd for Cl$_9$H$_{20}$O$_4$: C, 73.06; H, 6.45. Found: C, 73.12; H, 6.55.

29. $^1$H-NMR (CDCl$_3$, 300 MHz) δ 3.46 (d, J=1.8 Hz, 2H), 3.88 (s, 3H), 3.92 (s, 9H), 3.94 (s, 3H), 6.45 (t, J=1.9 Hz, 1H), 6.80 (s, 2H), 7.13 (s, 1H), 7.14 (s, 1H). $^{13}$C-NMR (CDCl$_3$, 75 MHz) δ 38.0, 56.1, 56.2, 61.0, 103.8, 104.5, 108.2, 129.2, 132.0, 136.5, 137.2, 137.5, 144.9, 147.4, 148.0, 153.4. HRMS (EI) M$^+$, calcd for C$_2$OH$_{22}$O$_5$ 342.1467, found 342.1464.

Example 5

Synthesis of Enediyne Ligands

1-[(3',4',5'-trimethoxyphenyl)-carbinol]-6-(tert-butyl-dimethylsilyl)-(Z)-3-ene-1,5-hexadiyne 34.

To a well-stirred, cooled (−78° C. dry ice/acetone) solution of tert-butyl[(Z)-3-hexene-1,5-diynyl]dimethylsilane (0.546 g, 2.87 mmol) in THF (20 mL) was added n-BuLi (2.5 M sol. in THF, 1.15 mL, 2.875 mmol). After stirring at −10° C. for 40 min, the temperature was returned to −78° C. and 3,4,5-trimethoxy-benzaldehyde (1.520 g, 6.590 mmol) in THF (5 mL) was added. After 12 h (−78° C. to r.t.) the reaction mixture was quenched with water and the product was isolated by extraction with EtOAC, followed by washing with brine and drying over $Na_2SO_4$. Removal of the solvent followed by purification by flash chromatography (80:20 hexanes:EtOAc) afforded the desired product (0.697 g, 1.80 mmol, 63%) as a yellow colored solid.

$^1$H-NMR (CDCl$_3$, 360 MHz) δ 6.79 (s, 2H, ArH), 5.91 (ABq, J=11.0 Hz, 10.9 Hz, 2H), 5.78 (s, br, —OH), 0.93 (s, 9H, —CH$_3$), 0.11 (d, J=2.3 Hz, 6H, —CH$_3$).

HRMS (EI) M$^+$ calcd for $C_{22}H_{30}O_4Si$ 386.1913, found 386.1913.

Anal. calcd for $C_{22}H_{30}O_4Si$: C, 68.36; H, 7.82. Found: C, 68.36; H, 7.92.

1-(3,4,5-trimethoxybenzoyl)-6-(tert-butyldimethylsilyl)-(Z)-3-ene-1,5-hexadiyne 35.

To a well-stirred solution of 1-[(3',4',5'-trimethoxyphenyl)-carbinol]-6-(tert-butly dimethylsilyl)-(Z)-3-ene-1,5-hexadiyne (0.697 g, 1.80 mmol.) in $CH_2Cl_2$ (30 mL) at 0° C. was added PCC (0.712 g, 3.30 mmol). The reaction mixture was stirred at room temperature for 3 h and then quenched with water and subjected to a standard work-up (EtOAc, brine, and drying over $Na_2SO_4$). Solvent removal followed by purification by column chromatography (initially 90:10 hexanes: EtOAc, increasing polarity of the solvent to 80:20 hexanes:EtOAc) gave the desired product (0.370 g, 0.962 mmol, 53%) as a yellow colored oil.

$^1$H-NMR (CDCl$_3$, 300 MHz) δ 7.44 (s, 2H, ArH), 6.13 (ABq, J=11.08 Hz, 10.98 Hz, 2H, —CH=CH—), 3.95 (s, 3H, —OCH$_3$), 3.94 (s, 3H, —OCH$_3$), 0.90 (s, 9H, —C(CH$_3$)$_3$), 0.11 (s, 6H, —Si(CH$_3$)$_2$).

$^{13}$C-NMR (CDCl$_3$, 90 MHz) δ 176.3, 153.0, 143.5, 132.0, 124.8, 117.6, 107.0, 105.3, 101.7, 92.7, 89.3, 60.9, 56.2, 25.9, 16.4, −5.0.

1-(3,4,5-trimethoxybenzoyl)-(Z)-3-ene-1,5-hexadiyne 30.

To a well-stirred solution of 1-(3,4,5-trimethoxybenzoyl)-6-(tert-butyl dimethyl silyl)-(Z)-3-ene-1,5-hexadiyne (0.070 g, 0.182 mmol) in $CH_2Cl_2$ (10 mL) at 0° C. under nitrogen, was added TBAF (1M in THF, 0.300 ml, 0.300 mmol). After stirring for 12 h, the reaction was quenched with water and subjected to a standard work-up protocol ($CH_2Cl_2$, brine, and drying over sodium sulfate). Solvent was removed under reduced pressure and the product was purified by column chromatography (90:10 hexanes:ethyl acetate) to afford enediyne 30 (0.027 g, 0.101 mmol, 56%) as an off-white solid which turned brownish in color on standing for several minutes.

$^1$H-NMR (CDCl$_3$, 300 MHz) δ 7.49 (s, 2H, ArH), 6.19 (ABq, J=11.12 Hz, 11.05 Hz, 2H, —CH=CH—), 3.95 (s, 3H, —OCH$_3$), 3.94 (s, 3H, —OCH$_3$), 3.57 (d, J=1.72 Hz, 1H, —CH).

$^{13}$C-NMR (CDCl$_3$, 90 MHz) δ 176.4, 153.0, 143.7, 131.8, 124.0, 119.2, 107.1, 92.7, 88.2, 87.7, 80.3, 60.9, 56.3.

HRMS (EI) M$^+$ calcd for $C_{16}H_{14}O_4$ 270.0892, found 270.0889.

Anal. calcd for $C_{16}H_{14}O_4$: C, 71.10; H, 5.22. Found: C, 71.20; H, 5.28.

Example 6

Synthesis of Phenolic Dihydronaphthalene Ligand

7-Amino-6-methoxy-1-tetralone

To a solution of acetic acid (20 mL) in $H_2O$ (100 mL), 7-nitro-6-methoxy-1-tetralone (2.21 g, 10.0 mmol) was added. The solution was heated to reflux for 1 hour, and then cooled down to rt. $NaHCO_3$ (60 mL, saturated solution) was added, and the mixture was partitioned between $CH_2Cl_2$ and water. The organic layer was dried over anhydrous sodium sulfate. After filtration, the organic layer was concentrated in vacuo to provide a red oil. 7-Amino-6-methoxy-1-tetralone (1.74 g, 9.1 mmol, 91%) was obtained following purification by column chromatography. $^1$H-NMR (CDCl$_3$, 300 MHz) 2.07 (m, 2H), 2.57 (t, J=6.5 Hz, 2H), 2.86 (t, J=6.0 Hz, 2H), 3.73 (b, 2H), 3.91 (s, 3H), 6.59 (s, 1H), 7.36 (s, 1H).

7-Hydroxy-6-methoxy-1-tetralone

7-Amino-6-methoxy-1-tetralone (0.96 g, 5.0 mmol) was dissolved in a mixture of sulfuric acid (96%, 2.1 mL) and $H_2O$ (3.9 mL). The solution was cooled to 0° C., and ice (5.0 g) was added resulting in the crystallization of a solid. A solution of NaNO$_2$ (0.48 g, 7 mmol) in $H_2O$ (5 mL) was added dropwise at 0° C. After the solution had been stirred for an additional 10 min, a few crystals of urea were added to decompose any excess sodium nitrite. To the cold solution of benzenediazonium bisulfate was added a solution of cupric nitrate trihydrate (19.0 g, 78.6 mmol) in $H_2O$ (150 mL) at 0° C. With vigorous stirring, cuprous oxide (0.72 g, 5.0 mmol) was added to the solution. The solution was stirred for 10 more min, and TLC was employed to monitor the reaction. The mixture was partitioned between ethyl ether and water. The organic layer was dried over anhydrous sodium sulfate, and after filtration, the organic layer was concentrated in vacuo to provide a yellow oil. 7-Hydroxy-6-methoxy-1-tetralone (0.22 g, 1.15 mmol, 23%) was obtained following purification by column chromatography. $^1$H-NMR (CDCl$_3$, 300 MHz) 2.09 (m, 2H), 2.59 (t, J=6.5 Hz, 2H), 2.88 (t, J=6.0 Hz, 2H), 3.95 (s, 3H), 5.60 (s, 1H), 6.66 (s, 1H), 7.56 (s, 1H). $^{13}$C-NMR (CDCl$_3$, 75 MHz) 23.6, 29.5, 38.6, 56.0, 109.6, 112.2, 126.5, 138.4, 144.4, 151.0, 197.2.

7-[(tertButyldimethylsilyl)oxy]-6-methoxy-1-tetralone

To a well-stirred solution of 7-Hydroxy-6-methoxy-1-tetralone (80.0 mg, 0.42 mmol) in $CH_2Cl_2$, was added Et$_3$N (47 mg, 0.46 mmol), followed by DMAP (5.1 mg, 0.042 mmol) and TBSCl (69 mg, 0.46 mmol) at 0° C. under dry nitrogen. After 2 h (at rt), the mixture was partitioned between $CH_2Cl_2$ and water. The organic layer was dried over anhydrous sodium sulfate, and after filtration, the organic layer was concentrated in vacuo to provide a yellow oil. 7-[(tertButyldimethylsilyl)oxy]-6-methoxy-1-tetralone (122 mg, 0.40 mmol, 95%) was obtained following purification by column chromatography. $^1$H-NMR (CDCl$_3$, 300 MHz) 0.15 (s, 6H), 0.99 (s, 9H),2.11 (m, 2H), 2.58 (t, J=6.1 Hz, 2H), 2.88 (t, J=6.0 Hz, 2H), 3.86 (s, 3H), 6.63 (s, 1H), 7.56 (s, 1H).

7-[(tertbutyldimethylsilyl)oxy]-1-hydroxy-6-methoxy-1-(3',4',5'-trimethoxyphenyl)-tetralin To a stirred solution of n-butyllithium (0.5 mL, 1.6 M in hexane solution, 0.80 mmol) in dry ether (20 mL), a solution of 3,4,5-trimethoxyphenylbromide (98.8 mg, 0.40 mmol) in ether (10 mL) was added under dry nitrogen at −78° C. The solution was stirred for 1 h in order to form 3,4,5-trimethoxyphenyllithum. 7-[(tertButyldimethylsilyl)oxy]-6-methoxy-1-tetralone (122 mg, 0.40 mmol) was added at −20° C, and stirring was continued for 2 h (−20° C.-rt). The mixture was partitioned between $CH_2Cl_2$ and water, and the organic layer was dried over anhydrous sodium sulfate. After filtration, the organic layer was concentrated in vacuo to provide a yellow oil. 7-[(tertbutyldimethylsilyl)oxy]-1-hydroxy-6-methoxy-1-(3',4',5'-trimethoxyphenyl)-tetralin (137 mg, 0.29 mmol, 73%) was obtained following purification by column chromatography. 1H-NMR (CDCl$_3$, 300 MHz) 0.04 (s, 6H), 0.89 (s, 9H), 1.80 (b, 1H), 2.11 (m, 4H), 2.81 (t, J=6.5, 2H), 3.79 (s, 6H), 3.81 (s, 3H), 3.84 (s, 3H), 6.49 (s, 1H), 6.56 (s, 2H), 6.59 (s, 1H). $^{13}$C-NMR (CDCl$_3$, 75 MHz) −4.3, 18.8, 20.2, 26.1, 29.9, 41.5, 55.8, 56.5, 61.2, 75.6, 104.2, 111.9, 121.2, 131.4, 134.2, 136.8, 143.8, 145.3, 150.9, 152.9.

7-Hydroxy-6-methoxy-1-(3',4',5'-trimethoxyphenyl)-3,4-dihydronaphthalene

To a solution of acetic acid (10 mL) in H$_2$O (60 mL), was added 7-[(tertbutyldimethylsilyl)oxy]-1-hydroxy-6-methoxy-1-(3',4',5'-trimethoxyphenyl)-tetralin (137 mg, 0.29 mmol). The solution was heated to reflux for 8 hour, and then cooled down to rt. NaHCO$_3$ (20 mL, saturated solution) was added, and the mixture was partitioned between CH$_2$Cl$_2$ and water. The organic layer was dried over anhydrous sodium sulfate, and after filtration, the organic layer was concentrated in vacuo to provide a yellow oil. 7-Hydroxy-6-methoxy-1-(3',4',5'-trimethoxyphenyl)-3,4-dihydronaphthalene (84.3 mg, 0.25 mmol, 86%) was obtained following purification by column chromatography. 1H-NMR (CDCl$_3$, 300 MHz) 2.37 (m, 2H), 2.78 (t, J=7.7 Hz, 2H), 3.84 (s, 6H), 3.88 (s, 3H), 3.91 (s, 3H), 5.41 (s, 1H), 5.98 (t, J=4.6 Hz, 1H), 6.54 (s, 2H), 6.68 (s, 1H), 6.81 (s, 1H).

Example 7

Inhibition of Tubulin Polymerization Assay

IC$_{50}$ values for tubulin polymerization were determined according to the procedure described in Bai et al.[29] Purified tubulin is obtained from bovine brain cells as described in Hamel and Lin.[30] Various amounts of inhibitor were preincubated for 15 minutes at 37° C. with purified tubulin. After the incubation period, the reaction was cooled and GTP was added to induce tubulin polymerization. Polymerization was then monitored in a Gilford spectrophotometer at 350 nm. The final reaction mixtures (0.25 ml) contained 1.5 mg/ml tubulin, 0.6 mg/ml microtubule-associated proteins (MAPs), 0.5 mM GTP, 0.5 mM MgCl$_2$, 4% DMSO and 0.1M 4-morpholineethanesulfonate buffer (MES, pH 6.4). IC$_{50}$ is the amount of inhibitor needed to inhibit tubulin polymerization 50% with respect to the amount of inhibition that occurs in the absence of inhibitor.

TABLE 1[31]

In Vitro Inhibition of Tubulin Polymerization.

| Compound | IC$_{50}$ ($\mu$M) |
| --- | --- |
| Phenolic Benzo[b]thiophene Ligand 2 | 0.5–0.75 |
| Benzo[b]thiophene Prodrug 3 | 1–4 |
| Tetralin 14A | 1–4 |
| Dihydronaphthalene 14B | 1–2 |
| Indane 23 | 10–40 |
| Indene 27 | 4–10 |
| 5-Amino-Dihydronaphthalene 15 | 0.5–1.0 |
| Dihydronaphthalene Phosphoramidate 16 | Inactive (>40) |
| Trimethoxybenzoyl Enediyne Analog 30 | 2–4 |
| Combretastatin A-4 | 1.2 ± 0.02 |

Example 8

Cytotoxicity Assay with P388 Leukemia Cells

One of the newly prepared compounds was evaluated for cytotoxic activity against P388 leukemia cells using an assay system similar to the National Cancer Institute procedure[23] described below and in Monks et al.[32] The ED$_{50}$ value (defined as the effective dosage required to inhibit 50% of cell growth) of the 5-amino-dihydronaphthalene derivative 15 was found to be 0.034 $\mu$g/mL, while the ED$_{50}$ for the phosphoramidate 16 was determined to be 20.4 $\mu$g/mL.

Example 9

Growth Inhibitory Activity Against Other Cancer Cell Lines

Several of the compounds described in this application were evaluated in terms of growth inhibitory activity against several human cancer cell lines, including pancreas, breast, CNS, lung-NSC, colon, and prostate lines. The assay used is described in Monks et al.[32] Briefly, the cell suspensions, diluted according to the particular cell type and the expected target cell density (5,000–40,000 cells per well based on cell growth characteristics), were added by pipet (100 $\mu$l) to 96-well microtiter plates. Inoculates were allowed a preincubation time of 24–28 hours at 37° C. for stabilization. Incubation with the inhibitor compounds lasted for 48 hours in 5% CO$_2$ atmosphere and 100% humidity. Determination of cell growth was done by in situ fixation of cells, followed by staining with a protein-binding dye, sulforhodamine B (SRB), which binds to the basic amino acids of cellular macromolecules. The solubilized stain was measured spectrophotometrically. The results of these assays are shown in Tables 2–6.[33] GI$_{50}$ is defined as the dosage required to inhibit tumor cell growth by 50%.

TABLE 2

Benzo[b]thiophene Phenol (BBT-OH) [2]

| Cell Type | Cell Line | GI$_{50}$($\mu$g/mL) |
| --- | --- | --- |
| CNS | SF-295 | 0.032 |
| Pancreas-a | BXPC-3 | 0.32 |
| Lung-NSC | NCI-H460 | 0.026 |
| Breast adn | MCF-7 | 0.035 |
| Colon | KM20L2 | 0.28 |
| Prostate | DU-145 | 0.034 |

Based on this somewhat limited data set, the average GI$_{50}$=2.5×10$^{-7}$ M, while the GI$_{50}$ against DU-145 prostate) is 7.1×10$^{-8}$ M.

TABLE 3

Dihydronaphthalene Ligand [14B]

| Cell Type | Cell Line | GI$_{50}$($\mu$g/mL) |
| --- | --- | --- |
| CNS | SF-295 | 0.0033 |
| Pancreas-a | BXPC-3 | 0.0054 |
| Lung-NSC | NCI-H460 | 0.0038 |
| Breast adn | MCF-7 | 0.0010 |
| Colon | KM20L2 | 0.0032 |
| Prostate | DU-145 | 0.0037 |

TABLE 4

5-Amino-Dihydronaphthalene Ligand [15]

| Cell Type | Cell Line | GI$_{50}$($\mu$g/mL) |
| --- | --- | --- |
| CNS | SF-295 | 0.0029 |
| Pancreas-a | BXPC-3 | 0.0034 |
| Lung-NSC | NCI-H460 | 0.0026 |
| Breast adn | MCF-7 | <0.0010 |
| Colon | KM20L2 | 0.0027 |
| Prostate | DU-145 | 0.0038 |

TABLE 5

Phosphoramidate [16]

| Cell Type | Cell Line | $GI_{50}(\mu g/mL)$ |
|---|---|---|
| CNS | SF-295 | 2.2 |
| Pancreas-a | BXPC-3 | 2.0 |
| Lung-NSC | NCI-H460 | 3.4 |
| Breast adn | MCF-7 | 3.0 |
| Colon | KM20L2 | 2.5 |
| Prostate | DU-145 | 2.8 |

TABLE 6

Trimethoxy-Endiyne Ligand [30]

| Cell Type | Cell Line | $GI_{50}(\mu g/mL)$ |
|---|---|---|
| Pancreas-a | BXPC-3 | 1.4 |
| Ovarian | OVCAR-3 | 0.53 |
| CNS | SF-295 | 1.7 |
| Lung-NSC | NCI-H460 | 1.7 |
| Pharynx-sqam | FADU | 0.95 |
| Prostate | DU-145 | 0.54 |

TABLE 7

Benzo[b]thiophene Prodrug 3

| Cell Type | Cell Line | $GI_{50}(\mu g/mL)$ |
|---|---|---|
| CNS | SF-295 | 0.11 |
| Pancreas-a | BXPC-3 | 0.35 |
| Lung-NSC | NCI-H460 | 0.035 |
| Breast and | MCF-7 | 0.028 |
| Colon | KM20L2 | 0.22 |
| Prostate | DU-145 | 0.045 |

* Based on this somewhat limited data set for BBT-P, the average $GI_{50} = 2.2 \times 10^{-7}$ M, while the $GI_{50}$ against MCF-7 (breast) is $4.6 \times 10^{-8}$ M.

TABLE 8

Compound 14A In Vitro Human Cancer Cell Line $GI_{50}$ ($\mu g/mL$)

| Cell Type | Cell Line | $GI_{50}(\mu g/mL)$ |
|---|---|---|
| Pancreas | BXPC-3 | 0.13 |
| Breast and | MCF-7 | 0.043 |
| CNS Gliobl | SF-268 | 0.67 |
| Lung-NSC | NCI-H460 | 0.16 |
| Colon | KM20L2 | 0.11 |
| Prostate | DU-145 | 0.38 |

TABLE 9

Indane 23 In Vitro Human Cancer Cell Line $GI_{50}(\mu g/mL)$

| Cell Type | Cell Line | $GI_{50}(\mu g/mL)$ |
|---|---|---|
| Pancreas -a | BXPC-3 | 0.54 |
| Breast and | MCF-7 | 0.44 |
| CNS Gliobl | SF-268 | 1.3 |
| Lung-NSC | NCI-H460 | 0.32 |
| Colon | KM20L2 | 0.84 |
| Prostate | DU-145 | 2.9 |

TABLE 10

Indene 27 In Vitro Human Cancer Cell Line $GI_{50}(\mu g/mL)$

| Cell Type | Cell Line | $GI_{50}(\mu g/mL)$ |
|---|---|---|
| Pancreas-a | BXPC-3 | 0.44 |
| Breast and | MCF-7 | 0.44 |
| CNS Gliobl | SF-268 | 1.7 |
| Lung-NSC | NCI-H460 | 0.97 |
| Colon | KM20L2 | 1.3 |
| Prostate | DU-145 | 2.5 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. For instance, in addition to the various metal salts described for the phosphates and phosphoramidates, any appropriate metal or non-metal cation and, in fact, any appropriately related salt construct can be employed without departing from the spirit and scope of the invention. For therapeutic and/or prophylactic anti-tumor purposes, the prodrugs of the present invention would be administered at a dosage of from about 5 mg/m$^2$ to about 100 mg/m$^2$ while intravascular infusion of the prodrug is preferred other modes of parenteral topical or enteral administration are usable under certain conditions.

The present invention also involves uses of the novel compounds described in manners relating to their effectiveness in tubulin polymerization and its subsequent vascular-related effects. Certainly a method for inhibiting tubulin polymerization is a part of the present invention. This involves contacting a tubulin containing system with an effective amount of a compound described in the present invention. This tubulin containing system may be in a tumor cell—thereby inhibiting neoplastic disease by administering an effective amount of a compound of the present invention. Patients may thus be treated. In cases of cancer treatment, it is believed that many neoplasias such as leukemia, lung cancer, colon cancer, thyroid cancer, CNS melanoma, ovarian cancer, renal cancer, prostate cancer and breast cancers may be effectively by the administration of an effective amounts of the compounds described in the present invention. Pharmaceutical preparations may be prepared by mixing the compounds of the present invention with a pharmaceutically acceptable carrier. This may be in tablet or intravascular form. In one important aspect, macular degeneration and related diseases of the eye where vascularization is involved, the method comprising administering an effective amount of a compound described in the present invention. Psoriasis may also be treated by administering an effective amount of the compound of the present invention. Likewise, any disease or condition caused or enhanced by undesired vascularization may be treated by administering an effective amount of the compound of the present invention.

In addition to the tumor selective vascular targeting and destruction capability attributed to the related compound combretastatin A-4, phosphate (CA-4P) this compound and also those of the present invention have potential application in the treatment of other diseases where the issue of vascularization is of great significance. Representative examples of these diseases include: diseases associated with ocular neovascularization (corneal and retinal), psoriasis and arthritis. (Personal communications from Oxigene, Inc. Watertown, Mass. has indicated results supporting this statement).

All such similar substitutes and modifications apparent to those skilled in the art are deemed to be within the spirit, scope and concept of the invention as defined by the appended claims.

REFERENCES

The following citations are incorporated in pertinent part by reference herein for the reasons cited.

1. Hamel, E., Antimitotic Natural Products and Their Interactions with Tubulin, *Medicinal Research Reviews,* 1996, 16, 207.
2. Gerwick, W. H.; Proteau, P. J.; Nagle, D. G.; Hamel, E.; Blokhin, A.; Slate, D. L., Structure of Curacin A, a Novel Antimitotic, Antiproliferative, and Brine Shrimp Toxic Natural Product from the Marine Cyanobacterium *Lyngbya majuscula, J Org. Chem.* 1994, 59, 1243.
3. Owellen, R. J.; Hartke, C. A.; Kickerson, R. M.; Hains, F. O., Inhibition of Tubulin-Microtubule Polymerization by Drugs of the Vinca Alkaloid Class, *Cancer Res.* 1976, 36, 1499.
4. Lavielle, G.; Havtefaye, P.; Schaeffer, C.; Boutin, J. A.; Cudennec, C. A.; Pierre, A., New α-Amino Phosphonic Acid Derivatives of Vinblastine: Chemistry and Antitumor Activity, *J. Med. Chem.* 1991, 34, 1998.
5. Kingston, D. G. I.; Samaranayake, G.; Ivey, C. A., The Chemistry of Taxol, a Clinically Useful Anticancer Agent, *J. Nat. Prod.* 1990, 53, 1.
6. Schiff, P. B.; Fant, J.; Horwitz, S. B., Promotion of Microtubule Assembly In Vitro by Taxol, *Nature,* 1979, 277, 665.
7. Swindell, C. S.; Krauss, N. E.; Horwitz, S. B.; Ringel, I., Biologically Active Taxol Analogs with Deleted A-ring Side Chain Substituents and Variable C-2' Configurations, *J. Med. Chem.* 1991, 34, 1176. (d) Parness, J.; Horwitz, S. B., Taxol Binds to Polymerized Tubulin In Vitro, *J. Cell Biol.* 1981, 91, 479.
8. Nakada, M.; Kobayashi, S.; Iwasaki, S.; Ohno, M., The First Total Synthesis of the Antitumor Macrolide Rhizoxin: Synthesis of the Key Building Blocks, *Tetrahedron Lett.* 1993, 34, 1035.
9. Nakada, M.; Kobayashi, S.; Iwasaki, S.; Ohno, M., The First Total Synthesis of the Antitumor Macrolide Rhizoxin, *Tetrahedron Lett.* 1993, 34, 1039.
10. Boger, D. L.; Curran, T. T., Synthesis of the Lower Subunit of Rhizoxin, *J. Org. Chem.* 1992, 57, 2235.
11. Rao, A. V. R.; Sharma, G. V. M.; Bhanu, M. N., Radical Mediated Enantioselective Construction of C-1 to C-9 Segment of Rhizoxin, *Tetrahedron Lett.* 1992, 33, 3907.
12. Kobayashi, S.; Nakada, M.; Ohno, M., Synthetic Study on an Antitumor Antibiotic Rhizoxin by Using an Enzymatic Process on Prochiral beta-Substituted Glutarates, *Pure Appl. chem.* 1992, 64, 1121.
13. Kobayashi, S.; Nakada, M.; Ohno, M., Synthetic Study on an Antitumor Antibiotic Rhizoxin by Using an Enzymatic Process on Prochiral beta-Substituted Glutarates *Indian J. Chem., Sect. B.* 1993, 32B, 159.
14. Rao, A. V. R.; Bhanu, M. N.; Sharma, G. V. M., Studies Directed Towards the Total Synthesis of Rhizoxin: Stereoselective Synthesis of C-12 to C-18 Segment, *Tetrahedron Lett.* 1993, 34, 707.
15. Lin, C. M.; Ho, H. H.; Pettit, G. R.; Hamel, E., Antimitotic Natural Products Combretastatin A-4 and Combretastatin A-2: Studies on the Mechanism of Their Inhibition of the Binding of Colchicine to Tubulin, *Biochemistry* 1989, 28, 6984.
16. Pettit, G. R.; Cragg, G. M.; Singh, S. B., Antineoplastic agents, 122. Constituents of Combretum caffrum, *J. Nat. Prod.* 1987, 50, 386. (c) Pettit, G. R.; Singh, S. B.; Cragg, G. M., Synthesis of Natural (−)-Combretastatin, *J. Org. Chem.* 1985, 50, 3404.
17. Pettit, G. R.; Cragg, G. M.; Herald, D. L.; Schmidt, J. M.; Lohavanijaya, P., Isolation and Structure of combretastatin, *Can, J. Chem.* 1982, 60, 1374.
18. Dorr, R. T.; Dvorakova, K.; Snead, K.; Alberts, D. S.; Salmon, S. E.; Pettit, G. R., Antitumor Activity of Combretastatin A4 Phosphate, a Natural Product Tubulin Inhibitor, *Invest. New Drugs,* 1996, 14, 131.
19. Hammonds, T. R.; Denyer, S. P.; Jackson, D. E.; Irving, W. L., Studies To Show That With Podophyllotoxin the Early Replicative Stages of Herpes Simplex Virus Type 1 Depend Upon Functional Cytoplasmic Microtubules, *J. Med. Microbiol.,* 1996, 45, 167.
20. Cortese, F.; Bhattacharyya, B.; Wolff, J., Podophyllotoxin as a Probe for the Colchicine Binding Site of Tubulin, *J. Biol. Chem.,* 1977, 252, 1134.
21. Nicolaou, K. C., Winssinger, N., Pastor, J., Ninkovic, S., Sarabia, F., He, Y., Vourloumis, D., Yang, Z., Oi, T., Giannakakou, P., Hamel, E., Sythesis of Epothilones A and B in Solid and Solution Phase, *Nature,* 1997, 387, 268–272.
22. Pettit, G. R., Kamano, Y., Herald, C. L., Tuinman, A. A., Boettner, F. E., Kizu, H., Schmidt, J. M., Baczynskyj, L., Tomer, K. B., Bontems, R. J., The Isolation and Structure of a Remarkable Marine Animal Antineoplastic Contituent: Dolastatin 10, *J. Am. Chem. Soc.,* 1987, 109, 6883–6885.
23. Pettit, G. R., Srirangam, J. K., Barkoczy, J., Williams, M. D., Boyd, M. R., Hamel, E., Pettit, R. K., Hogan F., Bai, R., Chapuis, J. C., McAllister, S. C., Schmidt, J. M., Antineoplastic Agents 365: Dolastatin 10 SAR Probes, *Anti-Cancer Drug Des.,* 1998, 13, 243–277.
24. Zhang, X.; Smith, C. D., Microtubule Effects of Welwistatin, a Cyanobacterial Indolinone that Circumvents Multiple Drug Resistance, *Molecular Pharmacology,* 1996, 49, 288.
25. Pettit, G. R., Toki, B., Herald, D. L., Verdier-Pinard, P., Boyd, M. R., Hamel, E., Pettit, R. K., Antineoplastic Agents 379. Synthesis of Phenstatin Phosphate, *J. Med. Chem.,* 1998, 41, 1688–1695.
26. Jiang, J. B.; Hesson, D. P.; Dusak, B. A.; Dexter, D. L.; Kang, G. J.; Hamel, E., Synthesis and Biological Evaluation of 2-Styrylquinazolin-4(3H)-ones, a New Class of Antimitotic Anticancer Agents Which Inhibit Tubulin Polymerization, *J. Med. Chem.* 1990, 33, 1721.
27. Cushman, M.; Nagarathnam, D.; Gopal, D.; Chakraborti, A. K.; Lin, C. M.; Hamel, E. Synthesis and Evaluation of Stilbene and Dihydrostilbene Derivatives as Potential Anticancer Agents That Inhibit Tubulin Polymerization, *J. Med. Chem.* 1991, 34, 2579.
28. Sawada, T.; Kato, Y.; Kobayashi, H.; Hashimoto, Y.; Watanabe, T.; Sugiyama, Y.; Iwasaki, S., A Fluorescent Probe and a Photoaffinity Labeling Reagent to Study the Binding Site of Maytansine and Rhizoxin on Tubulin, *Bioconjugate Chem.,* 1993, 4, 284.

29. Rao, S.; Horwitz, S. B.; Ringel, I., Direct Photoaffinity Labeling of Tubulin with Taxol, *J. Natl. Cancer Inst.*, 1992, 84, 785.
30. Chavan, A. J.; Richardson, S. K.; Kim, H.; Haley, B. E.; Watt, D. S., Forskolin Photoaffinity Probes for the Evaluation of Tubulin Binding Sites, *Bioconjugate Chem.* 1993, 4, 268.
31. Sawada, T.; Kobayashi, H.; Hashimoto, Y.; Iwasaki, S., Identification of the Fragment Photoaffinity-labeled with Azidodansyl-rhizoxin as Met-363-Lys-379 on beta-Tubulin, *Biochem. Pharmacol.* 1993, 45, 1387.
32. Staretz, M. E.; Hastie, S. B., Synthesis, Photochemical Reactions, and Tubulin Binding of Novel Photoaffinity Labeling Derivatives of Colchicine, *J. Org. Chem.* 1993, 58, 1589.
33. Hahn, K. M.; Hastie, S. B.; Sundberg, R. J., Synthesis and Evaluation of 2-Diazo-3,3,3-trifluoropropanoyl Derivatives of Colchicine and Podophyllotoxin as Photoaffinity Labels: Reactivity, Photochemistry, and Tubulin Binding, *Photochem. Photobiol.* 1992, 55, 17.
34. Sawada, T.; Hashimoto, Y.; Li, Y.; Kobayashi, H.; Iwasaki, S., Fluorescent and Photoaffinity Labeling Derivatives of Rhizoxin, Biochem. Biophys. *Res. Commun.* 1991, 178, 558.
35. Wolff, J.; Knipling. L.; Cahnmann, H. J.; Palumbo, G., Direct Photoaffinity Labeling of Tubulin with Colchicine, *Proc. Natl. Acad. Sci. U.S.A.* 1991, 88, 2820.
36. Floyd. L. J.; Barnes, L. D.; Williams, R. F., Photoaffinity Labeling of Tubulin with (2-Nitro-4-azidophenyl) deacetylcolchicine: Direct Evidence for Two Colchicine Binding Sites, *Biochemistry*, 1989, 28, 8515.
37. Safa, A. R.; Hamel, E.; Felsted, R. L., Photoaffinity Labeling of Tubulin Subunits with a Photoactive Analog of Vinblastine, *Biochemistry* 1987, 26, 97.
38. Williams, R. F.; Mumford, C. L.; Williams, G. A.; Floyd, L. J.; Aivaliotis, M. J.; Martinez, R. A.; Robinson, A. K.; Barnes, L. D., A Photoaffinity Derivative of Colchicine: 6-(4'-Azido-2'-nitrophenylamino) hexanoyldeacetylcolchicine. Photolabeling and Location of the Colchicine-binding Site on the alpha-subunit of Tubulin, *J. Biol. Chem.* 1985, 260, 13794.
39. Nogales, E., Wolf, S. G., and Downing, K. H., Structure α,β the α,β Tubulin Dimer by Electron Crystallography, *Nature*, 1998, 391, 199–203.
40. Shirai, R.; Tokuda, K.; Koiso, Y.; Iwasaki, S., Synthesis and Anti-Tubulin Activity of Aza-Combretastatins, *Biomedical Chem. Lett.* 1994, 699.
41. Jones, C. K.; Jevnikar, M. G.; Pike, A. J.; Peters, M. K.; Black, L. J.; Thompson, A. R.; Falcone, J. F.; Clemens, J. A., Antiestrogens. 2. Structure-Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity, *J. Med. Chem.* 1984, 27, 1057.
42. Grese, T. A.; Cho, S.; Finley, D. R.; Godfrey, A. G.; Jones, C. D.; Lugar III, C. W.; Martin, M. J.; Matsumoto, K.; Pennington, L. D.; Winter, M. A.; Adrian, M. D.; Cole, H. W.; Magee, D. E.; Phillips, D. L.; Rowley, E. R.; Short, L.; Glasebrook, A. L.; Bryant, H. R., Structure-Activity Relationships of Selective Estrogen Receptor Modulators: Modifications to the 2-Arylbenzothiophene Core of Raloxifene, *J. Med. Chem.*, 1997, 40, 146.
43. Palkowitz, A. D.; Glasebrook, A. L.; Thrasher, K. J.; Hauser, K. L.; Short, L. L.; Phillips, D. L.; Muehl, B. S.; Sato, M.; Shetler, P. K.; Cullinan, G. J.; Pell, T. R.; Bryant, H. U., Discovery and Synthesis of [6-Hydroxy-3-[4-[2-(1-piperidinyl)ethoxy]phenoxy]-2-(4-hydroxyphenyl)]benzo[b]thiophene: A Novel, Highly Potent, Selective Estrogen Receptor Modulator, *J. Med. Chem.*, 1997, 40, 1407.
44. Pinney, K. G., Anti-Mitotic Agents Which Inhibit Tubulin Polymerization, Baylor University, Application for United States Letters Patent, Filed, Mar. 6, 1997. U.S. Pat. No. 5,886,025. Issued, Mar. 23, 1999.
45. Kevin G. Pinney, Pilar Mejia, Vani P. Mocharla, Anupama Shirali, G. R. Pettit, Anti-Mitotic Agents Which Inhibit Tubulin Polymerization, PCT Application originally filed under the Patent Cooperation Treaty (Mar. 6, 1998 PCT/US98/04380) has now been filed (Sep. 6, 1999) as an actual patent application in the following countries: Australia, Canada, Europe (PCT member countries), Japan, Mexico, New Zealand, and the USA.
46. Mullica, D. F.; Pinney, K. G.; Mocharla, V. P.; Dingeman, K. M.; Bounds, A. D.; Sappenfield, E. L., Characterization and Structural Analyses of Trimethoxy and Triethoxybenzo[b]thiophene, *J. Chem. Cryst.*, 1998, 28, 289–295.
47. Pinney, K. G.; Dingeman, K. D.; Bounds, A. D.; Mocharla, V. P.; Pettit, G. R.; Bai, R.; Hamel, E., A New Anti-Tubulin Agent Containing the Benzo[b]thiophene Ring System, *Bioorganic and Medicinal Chemistry Letters*, 1999, 9, 1081–1086.
48. D'Amato, R. J.; Lin, C. M.; Flynn, E.; Folkman, J.; Hamel, E., 2-Methoxyestradiol, an endogenous mamalian metabolite, inhibits tubulin polymerization by interacting at the colchicine site, *Proc. Natl. Acad. Sci.* 1994, 91, 3964.
49. Cushman, M.; He, H-M.; Katzenellenbogen, J. A.; Lin, C. M.; Hamel, E., Synthesis, Antitubulin and Antimitotic Activity, and Cytotoxicity of Analogs of 2-Methoxyestradiol, an Endogenous Mammalian Metabolite of Estradiol That Inhibits Tubulin Polymerization by Binding to the Colchicine Binding Site, *J. Med. Chem.*, 1995, 38, 2041.
50. Hamel, E.; Lin, C. M.; Flynn, E.; D'Amato, R. J. D., Interactions of 2-Methoxyestradiol, and Endogenous Mammalian Metabolite, with Unpolymerized Tubulin and with Tubulin Polymers, *Biochemistry*, 1996, 35, 1304.
51. Cushman, M.; He, H.-M.; Katzenellenbogen, J. A.; Varma, R. K.; Hamel, E.; Lin, C. M.; Ram, S.; Sachdeva, Y. P., Synthesis of Analogs of 2-Methoxyestradiol with Enhanced Inhibitory Effects on Tubulin Polymerization and Cancer Cell Growth, *J. Med. Chem.*, 1997, (in press).
52. Boyd, M. R.; Paull, K. D., Some Practical Considerations and Applications of the National Cancer Institute In Vitro Anticancer Drug Discovery Screen, *Drug Development Research*, 1995, 34, 91.
53. Kevin G. Pinney, Feng Wang, and Maria del Pilar Mejia, Indole-Containing and Combretastatin-Related Anti-Mitotic and Anti-Tubulin Polymerization Agents, Provisional Patent Application (No. 60/154,639) filed on Sep. 17, 1999.
54. Dark, G. G., Hill, S. A., Prise, V. G., Tozer, G. M., Pettit, G. R., Chaplin, D. J., Combretastatin A-4, an Agent That Displays Potent and Selective Toxicity Toward Tumor Vasculature, *Cancer Res.*, 1997, 57, 1829–1834.
55. Chaplin, D. J.; Pettit, G. R.; Hill, S. A., *Anticancer Res.*, 1999, 19, 189.
56. Dark, G. G.; Hill, S. A.; Prise, V. E.; Tozer, G. M.; Pettit, G. R.; and Chaplin, D. J. *Cancer Res.*, 1997, 57, 1829, 57. Iyer, S.; Chaplin, D. J.; Rosenthal, D. S.; Boulares, A. H.; Li, L-Y; Smulson, M. E., *Cancer Res.*, 1998, 8, 4510.
58. Pettit, G. R.; Rhodes, M. R., *Anti-Cancer Drug Des.*, 1998, 13, 183.
59. Tozer, G. M.; Prise, V. E.; Wilson, J.; Locke, R. J.; Vojnovic, B.; Stratford, M. R. L.; Dennis, M. F.; Chaplin, D. J., *Cancer Res.*, 1999, 59, 1626.
60. Li, L.; Rojiani, A.; Siemann, D. W., Int. *J. Radiat. Oncol., Biol., Phys.*, 1998, 42, 899.
61. Maxwell, R. J.; Pharm, B.; Nielsen, F. U.; Breidahl, T.; Stodkilde-Jorgensen, H.; Horsman, M. R., *Int. J Radiat. Oncol., Biol., Phys.*, 1998, 42, 891.
62. Beauregard, D. A.; Thelwall, P. E.; Chaplin, D. J.; Hill, S. A.; Adams, G. E.; Brindle, K. M., *Br. J. Cancer*, 1998, 77, 1761.
63. Myers, A. G.; Tom, N. J.; Fraley, M. E.; Cohen, S. B.; Madar, D. J. *J. Am. Chem. Soc.*, 1997, 119, 6072–6094.
64. Churcher, I.; Hallett, D.; Magnus, P. *J.Am. Che. Soc.*, 1998, 120, 10350–10358.
65. Clive, D. L. J.; Bo, Y.; Tao, Y.; Daigneault, S.; Wu, Y. J.; Meignan, G. *J. Am. Chem. Soc.*, 1998, 120, 10332–10349.
66. Bai, R.; Schwartz, R. E.; Kepler, J. A.; Pettit, G. R.; Hamel, E., Characterization of the Interaction of Cryptophycin with Tubulin: Binding in the Vinca Domain, Competitive Inhibition of Dolastatin 10 Binding, and an Unusual Aggregation Reaction, *Cancer Res.*, 1996, 56, 4398–4406.
67. Hamel, E.; Lin, C. M., Separation of Active Tubulin and Microtubule-Associated Proteins by Ultracentrifugation and Isolation of a Component Causing the Formation of Microtubule Bundles, *Biochemistry*, 1984, 23, 4173–4184.
68. Tubulin polymerization studies carried out through a collaborative effort with Dr. Ernest Hamel, National Cancer Institute, National Institutes of Health.
69. Monks, A.; Scudiero, D.; Skehan, P.; Shoemaker, R.; Paull, K.; Vistica, D.; Hose, C.; Langley, J.; Cronise, P.; Vaigro-Wolff, A.; Gray-Goodrich; Campbell; Mayo; Boyd, M., Feasibility of a High-Flux AnticancerDrug Screen Using a Diverse Panel of Cultured Human Tumor Cell Lines, *J. Natl. Cancer Inst.*, 1991, 83, 757–766.
70. Cell line studies carried out through a collaborative effort with Professor George R. Pettit, Arizona State University.
71. Flynn, B. E.; Verdier-Pinard, P.; Hamel, E., A Novel Palladium-Mediated Coupling Approach to 2,3-Disubstituted Benzo[b]thiophenes and Its Application to the Synthesis of Tubulin Binding Agents, *Organic Letters*, 2001, 3, 651–654.
72. Pettit, G. R.; Lippert III, J. W., Antineoplastic agents 429. Syntheses of the combretastatin A-1 and combretastatin B-1 prodrugs, *Anti-Cancer Drug Design*, 2000, 15, 203–216.

What is claimed is:

1. A compound of the structure:

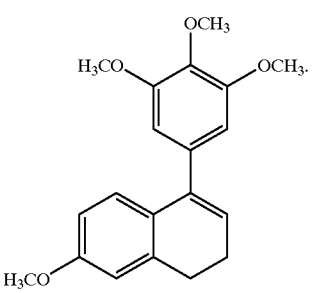

2. A compound of the structure:

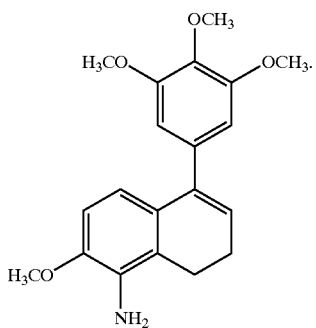

3. A compound of the structure:

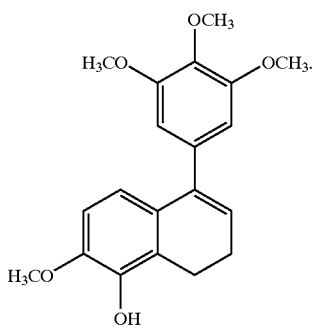

4. A compound of the structure:

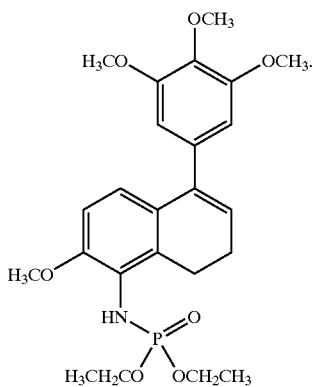

5. A compound of the structure:

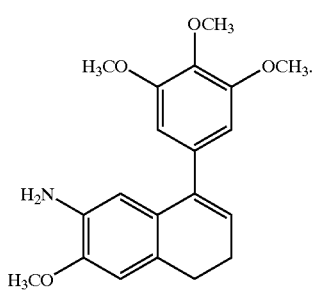

6. A compound of the structure:

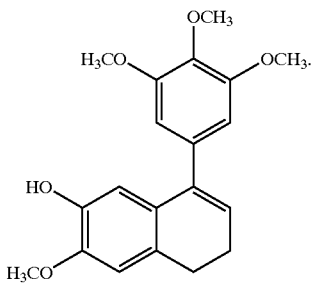

7. A compound of the structure:

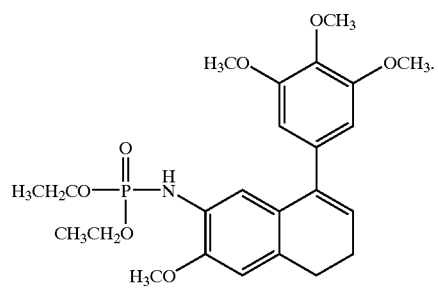

8. A compound of the structure:

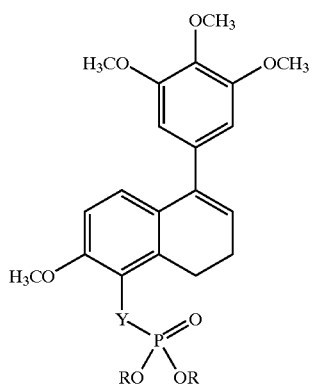

wherein
Y is either NH, S, or O, and R is an alkyl, branched alkyl, benzyl or aryl substituent (the two R groups are the same or different), or a metal cation.

9. A compound of the structure:

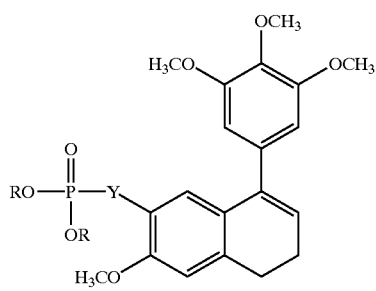

wherein
Y is either NH, S, or O, and R is an alkyl, branched alkyl, benzyl or aryl substituent (the two R groups are the same or different), or a metal cation.

10. A compound of the structure:

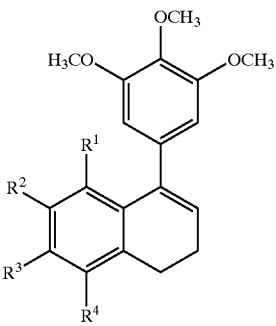

wherein
$R^1$ through $R^4$ contain at least two phenolic moieties (—OH) or or at least two amino groups ($NH_2$, NHR, or $NR^6R^7$) where $R^6$ and $R^7$ are the same or different alkyl, branched alkyl, benzyl, or aryl substituent, or $R^1$ through $R^4$ contain one phenolic moiety and one amino moiety, while the remaining $R^1$ through $R^4$ one is a methoxy (—$OCH_3$) and one is a hydrogen atom.

11. A compound of the structure:

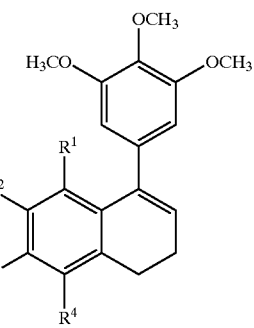

wherein
$R^1$ through $R^4$ contain at least two phosphate esters (—OP(O)($O^-M^+$)$_2$) or two phosphoramidates moieties (—NHP(O)($O^-M^+$)$_2$) where M is an alkali metal cation; or (—NHP(O)(OR)$_2$) where R chosen to be any appropriate alkyl, branched alkyl, benzyl, or aryl substituent (the two R groups are the same or different), or $R^1$ through $R^4$ contain one phosphate ester and one phosphoramidate, while of the remaining $R^1$ through $R^4$ one is a methoxy group (—$OCH_3$) and one is a hydrogen atom.

12. A compound of the structure:

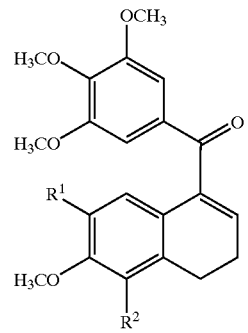

wherein
If $R^1$ is —OH or —$NH_2$ then $R^2$ is H, and if $R^2$ is —OH or —$NH_2$ then $R^1$ is H.

13. A compound of the structure:

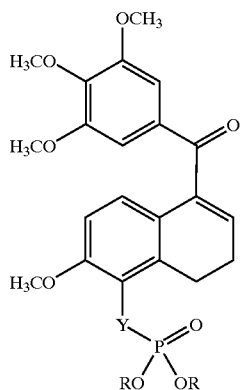

wherein

Y is either NH, S, or O, and R is an alkyl, branched alkyl, benzyl or aryl substituent (the two R groups may be the same or different), or a metal cation.

14. A compound of the structure:

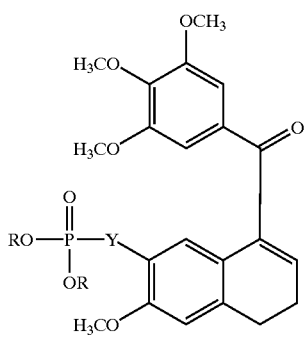

wherein

Y is either NH, S, or O, and R is an alkyl, branched alkyl, benzyl or aryl substituent (the two R groups may be the same or different), or a metal cation.

15. A compound of the structure:

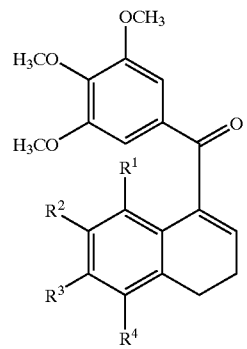

wherein $R^1$ through $R^4$ contain at least two phenolic moieties (—OH) or at least two amino group ($NH_2$, NHR, or $NR^6R^7$) where $R^6$ and $R^7$ are the same or different alkyl, branched alkyl, benzyl, or aryl substituents, where $R^1$ through $R^4$ contain one phenolic moiety and one amino moiety, while of the remaining $R^1$ through $R^4$ one is a methoxy group (—$OCH_3$) and one is a hydrogen atom.

16. A compound of the structure:

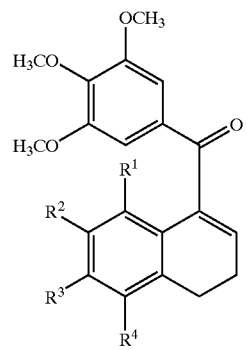

wherein $R^1$ through $R^4$ contain at least two phosphate ester (—OP(O)($O^-M^+$)$_2$) or two phosphoramidate moieties (—NHP(O)($O^-M^+$)2) where M is an alkali metal cation; or (—NHP(O)(OR)$_2$) where R is an alkyl, branched alkyl, benzyl or aryl substituent (the two R groups are the same or different), where $R_1$ through $R^4$ contain one phosphate ester and one phosphoramidate, while of the remaining $R^1$ through $R^4$ one is a methoxy group (—$OCH_3$) and one is a hydrogen atom.

* * * * *